United States Patent
Faybishenko et al.

(10) Patent No.: US 9,131,893 B2
(45) Date of Patent: Sep. 15, 2015

(54) HEALTH DIAGNOSTIC SYSTEMS AND METHODS

(71) Applicant: Pixie Scientific, LLC, New York, NY (US)

(72) Inventors: Yaroslav Faybishenko, New York, NY (US); Boris Faybishenko, Berkeley, CA (US)

(73) Assignee: Pixie Scientific, LLC, New York, NY (US)

(*) Notice: Subject to any disclaimer, the term of this patent is extended or adjusted under 35 U.S.C. 154(b) by 0 days.

(21) Appl. No.: 14/065,360

(22) Filed: Oct. 28, 2013

(65) Prior Publication Data

US 2014/0121487 A1    May 1, 2014

Related U.S. Application Data

(60) Provisional application No. 61/718,970, filed on Oct. 26, 2012.

(51) Int. Cl.
  *A61B 5/1455*    (2006.01)
  *A61B 5/00*    (2006.01)
  (Continued)

(52) U.S. Cl.
  CPC ............ *A61B 5/6808* (2013.01); *A61B 5/0013* (2013.01); *A61B 5/0077* (2013.01);
  (Continued)

(58) Field of Classification Search
  CPC .. A61B 5/6808; A61B 5/0013; A61B 10/007; A61B 5/742; A61B 5/7221; A61B 5/0022; A61B 5/0077; A61B 5/14532; A61B 5/14546; A61B 5/6898; A61B 5/150358; A61B 5/14517; A61B 10/0038
  USPC ............ 600/300, 310; 604/361, 362; 128/903; 382/128, 162
  See application file for complete search history.

(56) References Cited

U.S. PATENT DOCUMENTS

| | | |
|---|---|---|
| 3,146,070 A | 8/1964 | Collins |
| 4,318,709 A | 3/1982 | Falb et al. |

(Continued)

FOREIGN PATENT DOCUMENTS

| | | |
|---|---|---|
| DE | 29709497 U1 | 9/1997 |
| DE | 19837678 A1 | 3/2000 |

(Continued)

OTHER PUBLICATIONS

May 2, 2014, International Search Report of the International Search Authority from the U.S Receiving Office, in PCT/US2013/067150, which is the international application to this U.S. application.

(Continued)

*Primary Examiner* — Eric Winakur
(74) *Attorney, Agent, or Firm* — Kolisch Hartwell, P.C.

(57) ABSTRACT

A health monitoring system, and methods of use and manufacture thereof are disclosed. The health monitoring system may include a computing system and a diagnostic test coupled to a diaper. The diagnostic test may include one or more sensors configured to produce a visual indication of one or more analytes contained in a sample produced by a subject. The diagnostic test may include a machine-readable code. The computing system may be configured to read the machine-readable code to allow an application running on the computing system to automatically perform at least one task related to a production of a data point based on the visual indication. The health monitoring system may aid in identifying a potential abnormal health condition of the subject by providing automatic longitudinal analysis of analytes contained in samples produced by the subject over a period of time.

32 Claims, 22 Drawing Sheets

(51) Int. Cl.
*A61B 5/15* (2006.01)
*A61B 10/00* (2006.01)
*A61B 5/145* (2006.01)

(52) U.S. Cl.
CPC ....... *A61B5/14507* (2013.01); *A61B 5/150358* (2013.01); *A61B 5/150969* (2013.01); *A61B 5/7221* (2013.01); *A61B 10/007* (2013.01); *A61B 10/0038* (2013.01); *A61B 5/0022* (2013.01); *A61B 5/14517* (2013.01); *A61B 5/14532* (2013.01); *A61B 5/14546* (2013.01); *A61B 5/6898* (2013.01); *A61B 5/742* (2013.01); *A61B 5/7435* (2013.01); *A61B 2562/12* (2013.01); *A61B 2576/02* (2013.01)

(56) References Cited

U.S. PATENT DOCUMENTS

| | | | |
|---|---|---|---|
| 5,516,700 | A | 5/1996 | Smith et al. |
| 5,922,283 | A | 7/1999 | Hsu |
| 5,959,535 | A | 9/1999 | Remsburg |
| 6,060,256 | A | 5/2000 | Everhart et al. |
| 6,149,865 | A | 11/2000 | Hsu |
| 6,186,991 | B1 | 2/2001 | Roe et al. |
| 6,203,496 | B1 * | 3/2001 | Gael et al. ............ 600/362 |
| 6,436,055 | B1 | 8/2002 | Roe |
| 6,479,727 | B1 | 11/2002 | Roe |
| 6,862,466 | B2 * | 3/2005 | Ackerman ............ 600/347 |
| 6,981,951 | B1 | 1/2006 | Rahe |
| 7,176,344 | B2 | 2/2007 | Gustafson et al. |
| 7,187,790 | B2 * | 3/2007 | Sabol et al. ............ 382/128 |
| 7,314,752 | B2 | 1/2008 | Kritzman et al. |
| 7,365,238 | B2 | 4/2008 | Diehl et al. |
| 7,541,177 | B2 | 6/2009 | Kritzman et al. |
| 7,619,033 | B2 | 11/2009 | Calhoun et al. |
| 7,947,467 | B2 | 5/2011 | Kritzman et al. |
| 8,044,257 | B2 | 10/2011 | Song |
| 8,196,809 | B2 | 6/2012 | Thorstensson |
| 8,217,217 | B2 | 7/2012 | Diehl et al. |
| 8,244,638 | B2 * | 8/2012 | Agarwal et al. ............ 705/44 |
| 8,273,939 | B2 * | 9/2012 | Klofta et al. ............ 604/361 |
| 8,278,497 | B2 | 10/2012 | Klofta et al. |
| 8,293,967 | B2 | 10/2012 | Klofta et al. |
| 8,506,901 | B2 | 8/2013 | Chen et al. |
| 2004/0220538 | A1 | 11/2004 | Panopoulos |
| 2005/0101841 | A9 | 5/2005 | Kaylor et al. |
| 2008/0266117 | A1 | 10/2008 | Song et al. |
| 2012/0063652 | A1 | 3/2012 | Chen et al. |
| 2012/0106811 | A1 | 5/2012 | Chen et al. |
| 2012/0173249 | A1 | 7/2012 | Popp et al. |
| 2012/0201437 | A1 * | 8/2012 | Ohnemus ............ 382/128 |
| 2013/0126347 | A1 * | 5/2013 | Krassnitzer et al. ..... 204/298.16 |
| 2013/0211731 | A1 * | 8/2013 | Woltman ............ 702/21 |
| 2013/0273666 | A1 | 10/2013 | Chen et al. |
| 2014/0294265 | A1 | 10/2014 | Chen et al. |

FOREIGN PATENT DOCUMENTS

| | | |
|---|---|---|
| WO | 9424557 A1 | 10/1994 |
| WO | 0065348 A2 | 11/2000 |
| WO | 2006047815 A1 | 11/2006 |
| WO | 2007073139 A1 | 6/2007 |
| WO | 2009121043 A2 | 10/2009 |

OTHER PUBLICATIONS

May 2, 2014, Written Opinion of the International Search Authority from the U.S Receiving Office, in PCT/US2013/067150, which is the international application to this U.S. application.

Apr. 28, 2015, International Preliminary Report on Patentability, from The International Bureau of WIPO, in PCT/US2013/067150, which is the international application to this U.S. application.

* cited by examiner

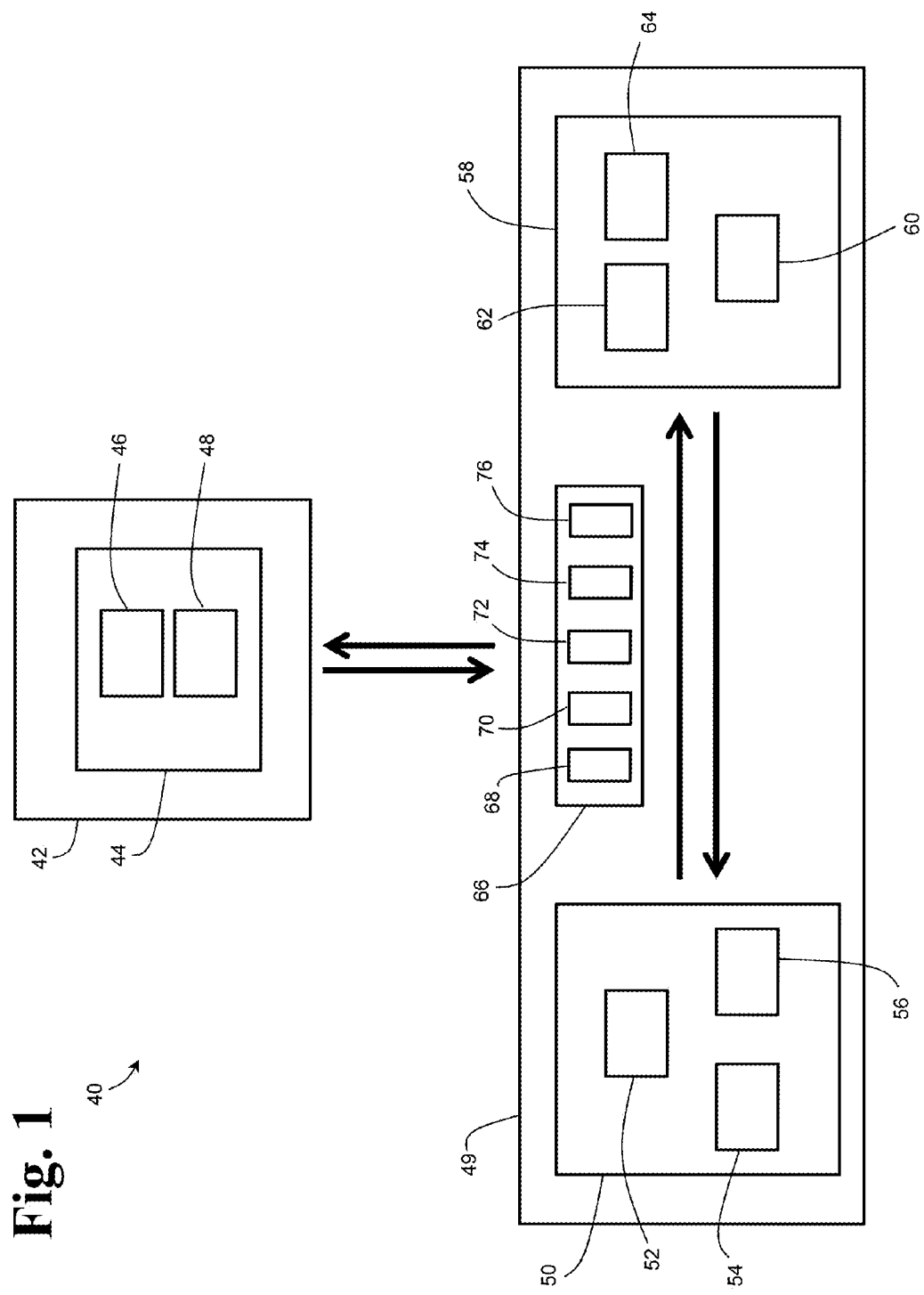

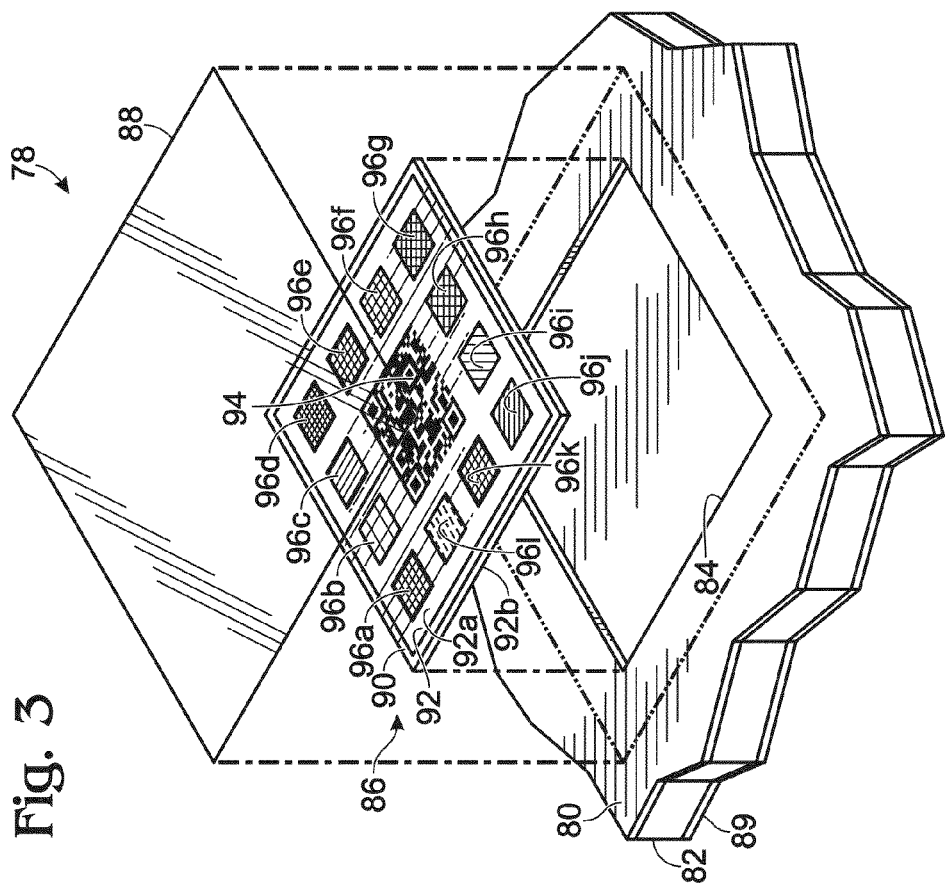
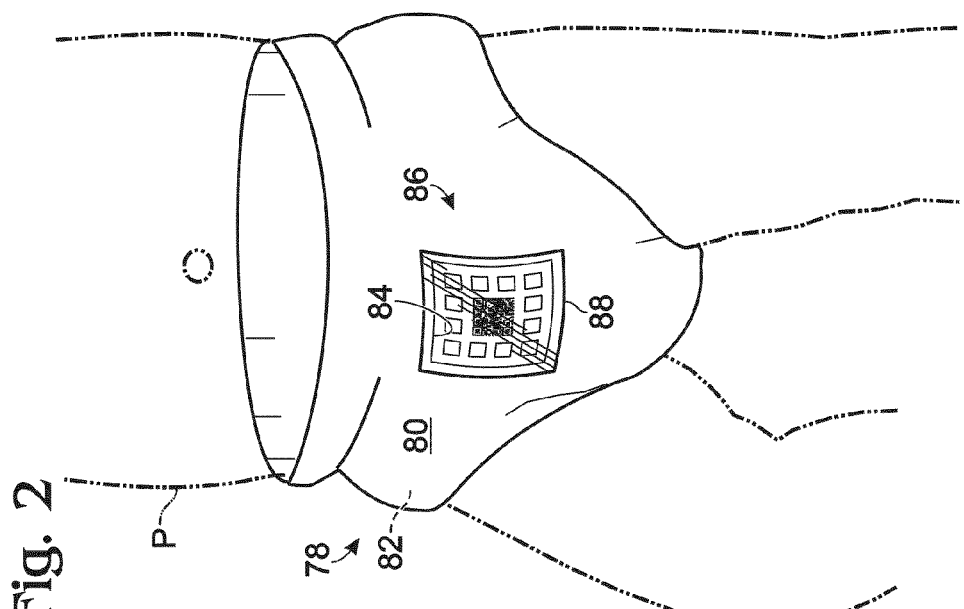

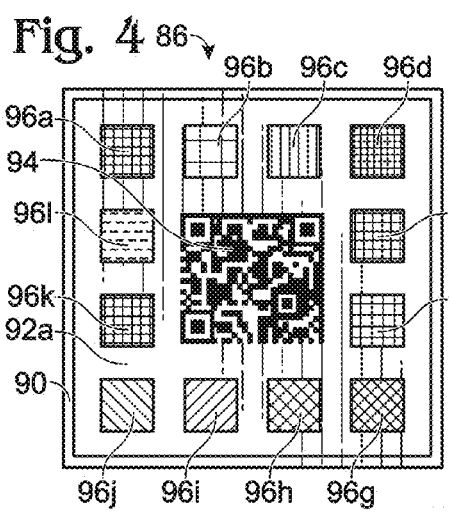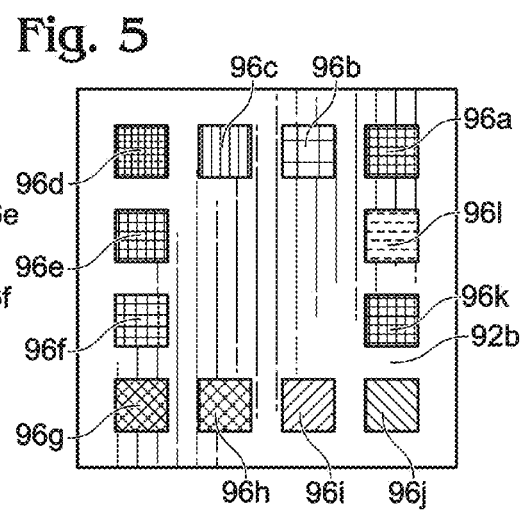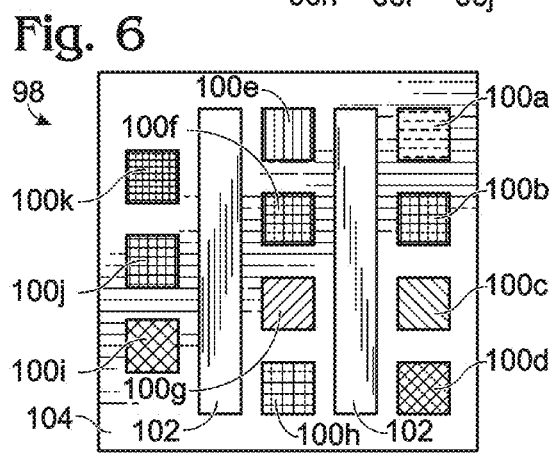

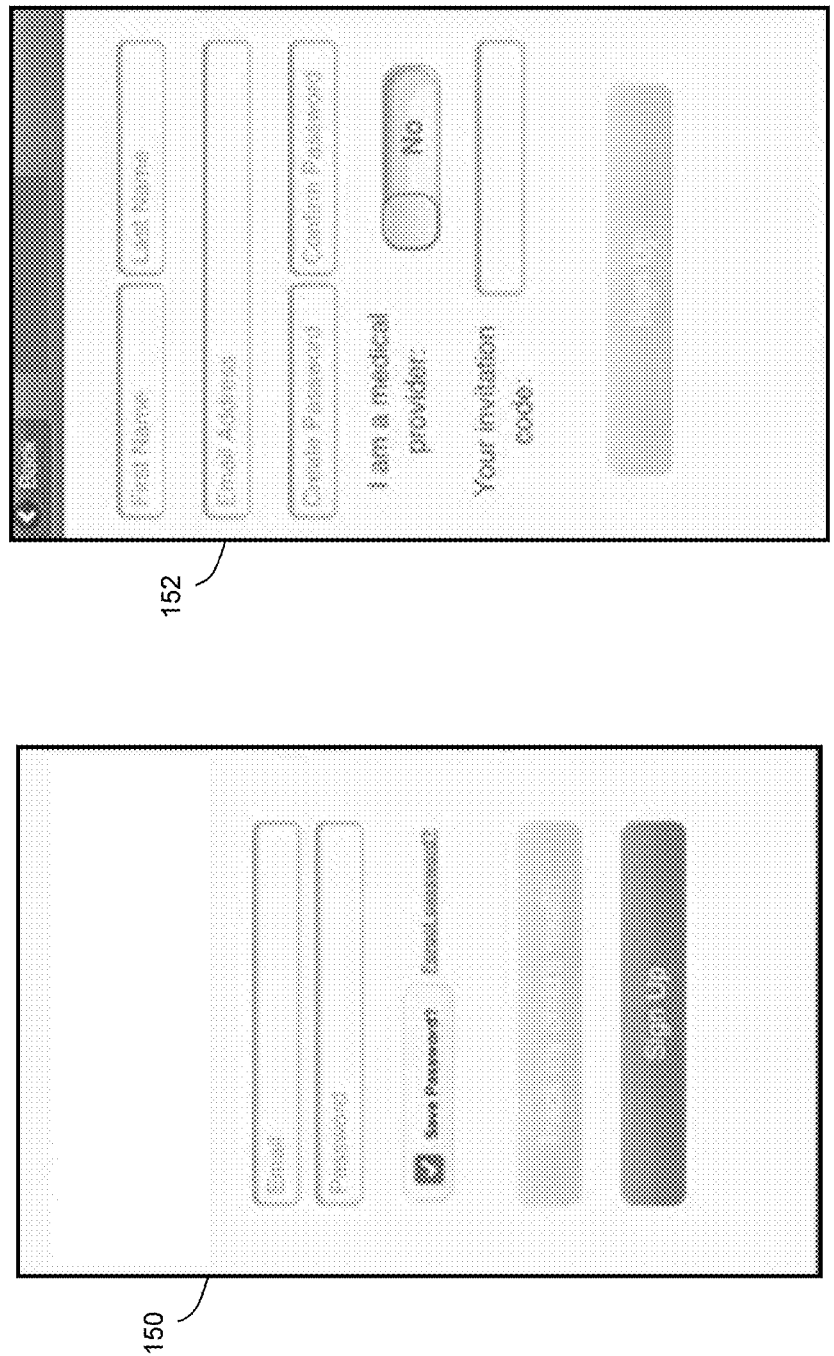

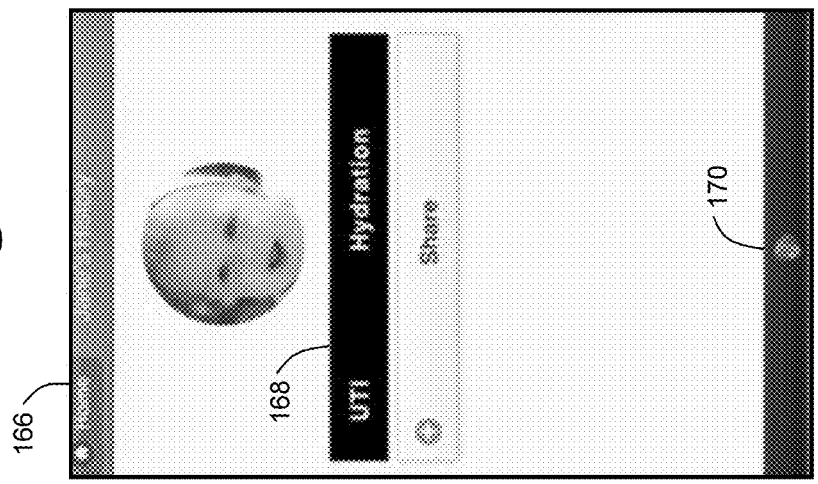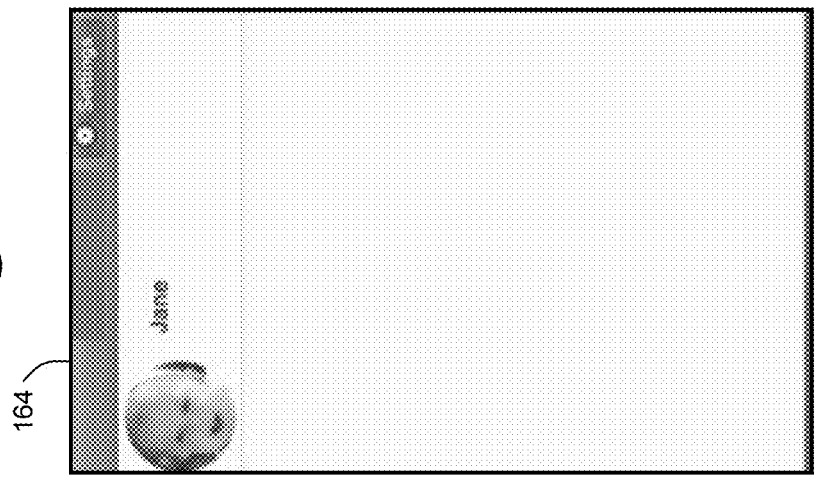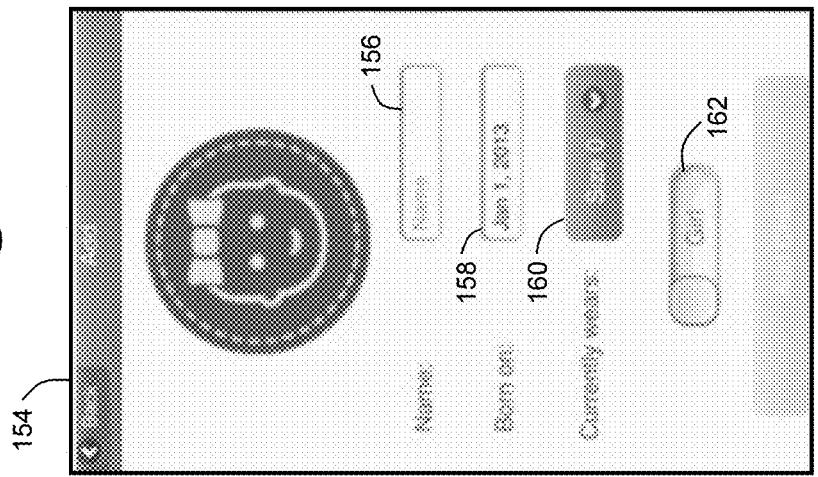

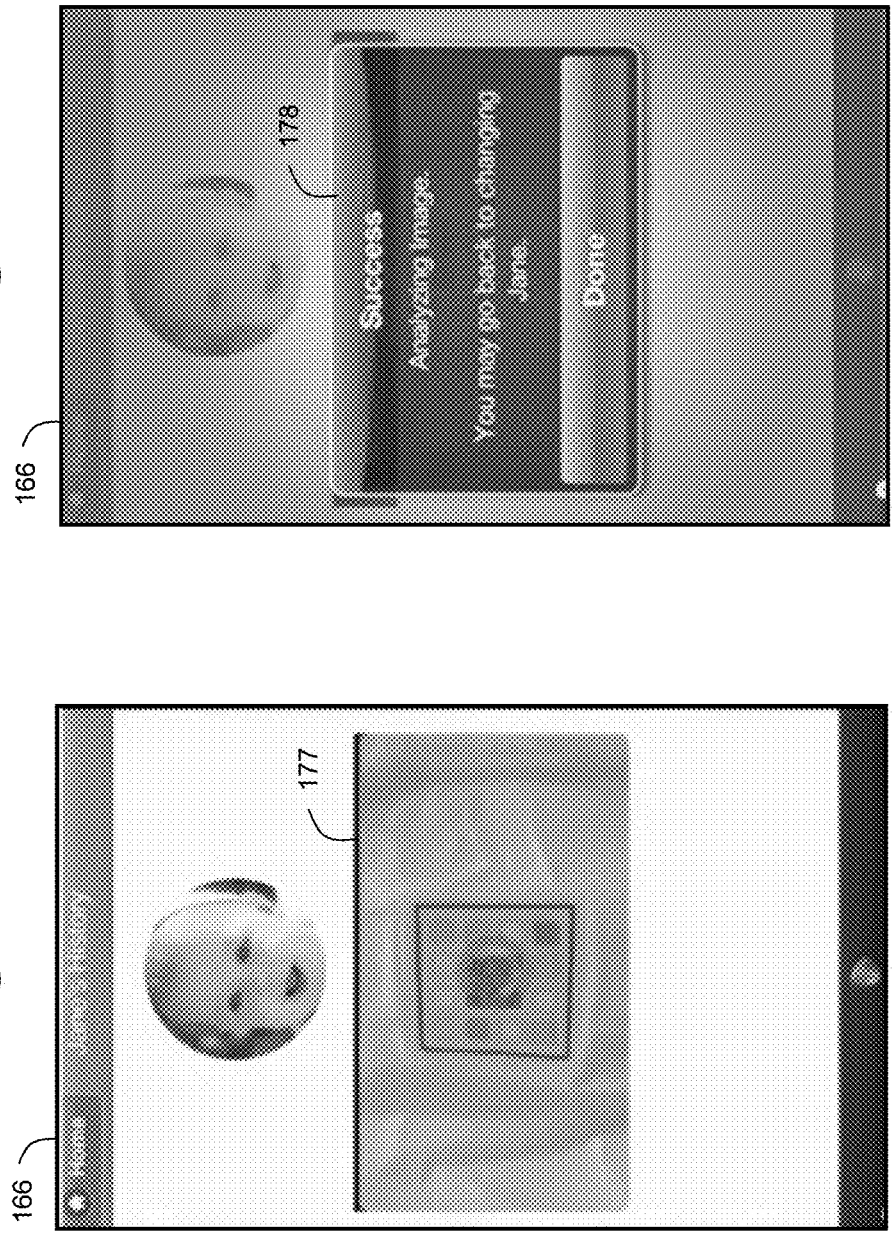

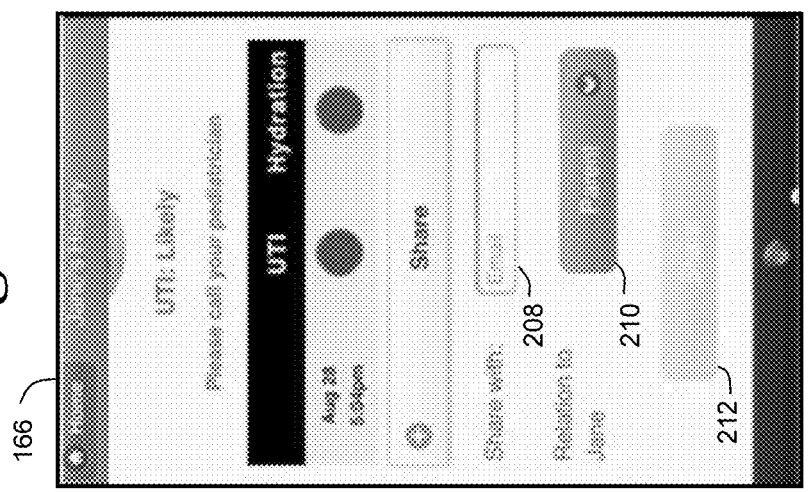
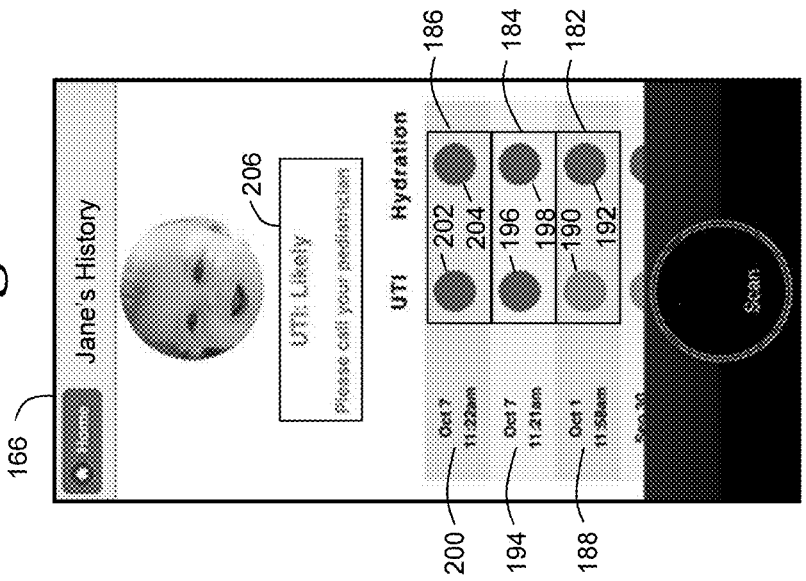
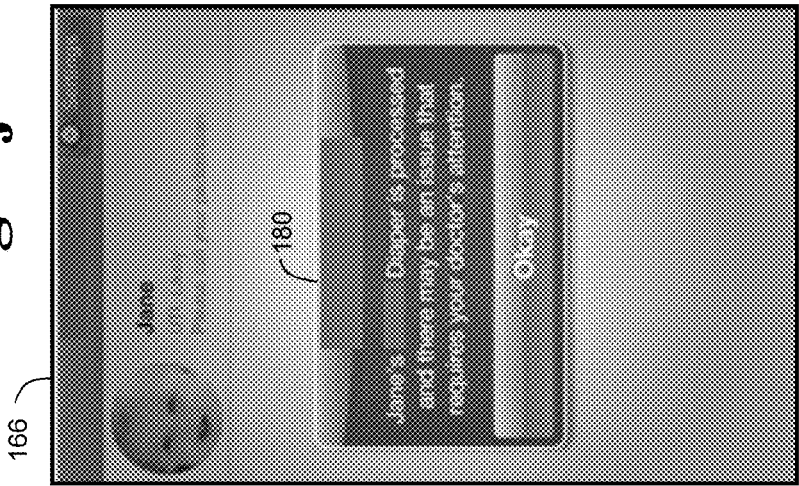

HEALTH DIAGNOSTIC SYSTEMS AND METHODS

CROSS-REFERENCE TO RELATED APPLICATION

This application claims priority to U.S. Provisional Patent Application Ser. No. 61/718,970, filed Oct. 26, 2012, which is hereby incorporated by reference in its entirety for all purposes.

INTRODUCTION

Although urine content potentially carries evidence of developing under-hydration or infection, or of endocrine or metabolic system problems, people and physicians have no easy method to track and analyze changes in urine content over time. People and physicians therefore currently rely on visible symptoms to prompt urine analysis or blood tests. Thus, in today's practice urine analysis is most often used to confirm symptom-based diagnosis, rather than as initial identification of disease. Some conditions, like diabetic ketoacidosis, show visible symptoms only when a person's condition may already warrant an emergency visit to a physician. Other conditions, like urinary tract infection, may not show visible symptoms and result in renal scarring, which may not manifest itself in health problems until many years later. Urine content is also ideally suited for epidemiological studies to rapidly identify problems prevalent in specific geographies, but difficulty of sample collection prevents acceleration of research in this area.

Existing diagnostic systems rely on urinalysis strips being dipped into a urine sample. Data from urine analysis strips generally has to be manually entered into a database and thus is rarely analyzed at a later point in time or compared with future readings. Diapers exist with embedded sensors that are only capable of detecting wetness. They transmit that information to a receiving system. The receiving system is only capable of alerting a caregiver of a one-time event.

Embodiments of systems and methods of the present disclosure may enable monitoring of urine content, as well as trend and statistical analysis that can identify slow changes in hydration and kidney function, impending infections, and other potential metabolic and endocrine disease states that, for example, can only be identified with multiple data points. Other data such as medical and family history as well as current variables such as age, temperature, and/or other current markers may be used to supplement trend and statistical analysis. Also tracking geographic location may enable identification of potential disease epidemics. As stated above, although urine content potentially carries evidence of developing under-hydration or infection, or of endocrine or metabolic system problems, people and physicians have no easy way to track and analyze changes in urine content over time. It is also currently difficult to conduct epidemiological studies based on urine content.

BRIEF DESCRIPTION OF THE DRAWINGS

FIG. 1 depicts a diagnostic system, according to aspects of the present disclosure.

FIG. 2 depicts an embodiment of a sample collection device of the diagnostic system of FIG. 1.

FIG. 3 is a partially exploded sectional view of a portion of the sample collection device of FIG. 2.

FIG. 4 is a top plan view of a diagnostic test of the sample collection device of FIG. 2.

FIG. 5 is a bottom plan view of the diagnostic test of FIG. 4.

FIG. 6 is a top plan view of another embodiment of a diagnostic test, according to aspects of the present disclosure.

DETAILED DESCRIPTION

Figure 7:
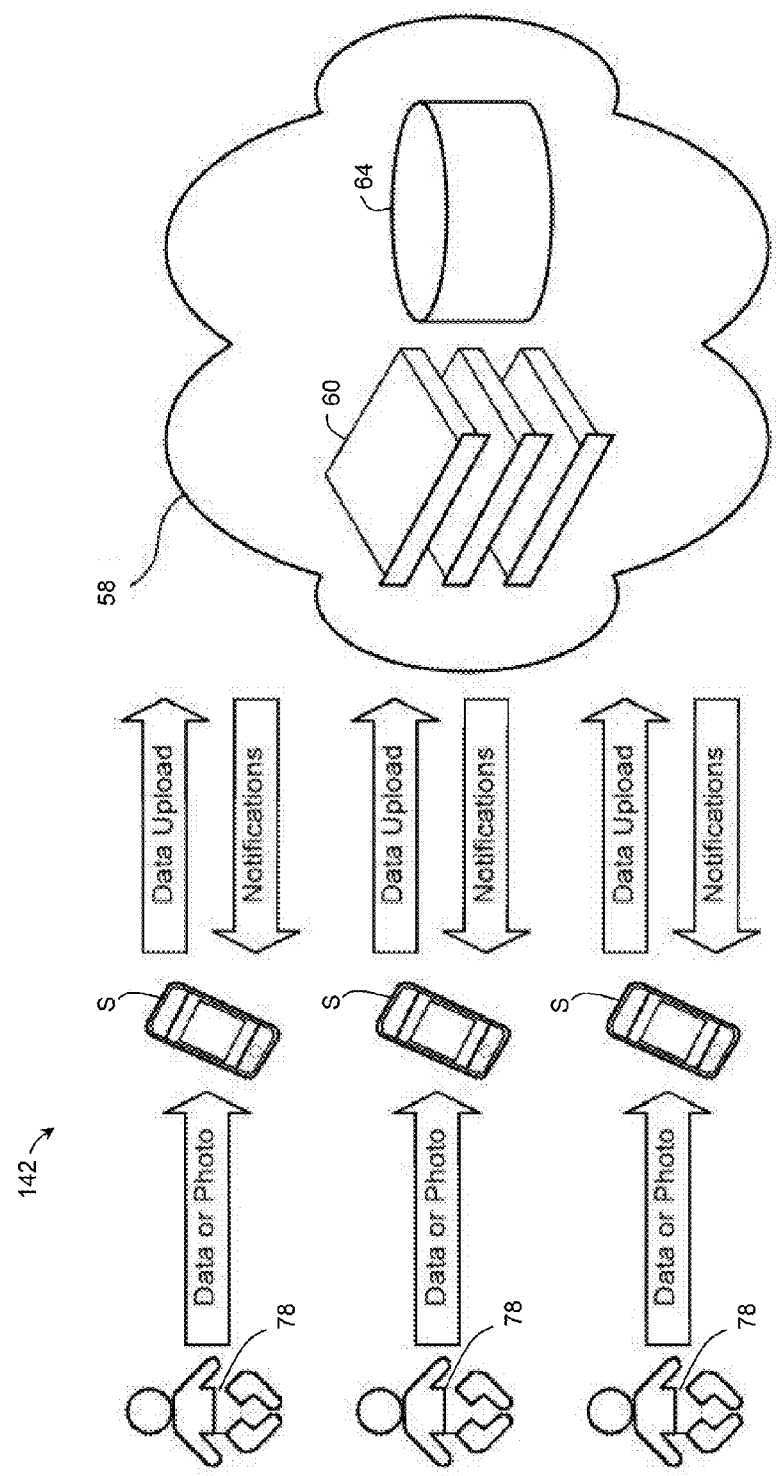
FIG. 7 depicts a first illustrative embodiment of the diagnostic system of FIG. 1.

The present disclosure is directed to diagnostic systems and methods, which may include a sample collection device and a computing system configured to acquire, transmit, process, analyze, and/or store diagnostic data from the sample collection device.

Embodiments of Health Diagnostic Systems

FIG. 1 depicts a diagnostic system (or health monitoring system), generally indicated at 40, according to aspects of the present disclosure. Diagnostic system 40 may include a sample collection device 42, which may be any suitable device for at least partially collecting a sample (e.g., bodily waste) from a patient, such as urine or any other suitable sample for a diagnostic such as feces, blood, and/or sweat. Sample collection device 42 may be wearable, such as a diaper for a human infant, toddler, child, or adult or a pet animal, or may be an incontinence pad which may be inserted into and/or worn under the patient's underwear (e.g., between the underwear and the patient's body). It should be appreciated that the title of patient is intended to include all suitable subjects (e.g., humans, animals, etc.) and is thus not limited to hospital use or use by medical professionals.

Diagnostic system 40 may include a sensor unit or diagnostic test 44, which may be coupled to or releasably coupled to sample collection device 42, such that sensor unit 44 may be exposed to a sufficient sample for performing a diagnostic, such as a sufficient amount of urine. Sensor unit 44 may include one or more sensors or diagnostic sensors 46, such as filter paper, and one or more controls 48, such as a non-absorbent color reference material. The one or more sensors may be configured to produce diagnostic data (e.g., a visual indication) based on one or more analytes contained in the sample.

Control 48 may be configured to one or more diagnostic sensors 46 to provide information related to validity, accuracy, and/or normalization of content analysis (e.g., detection of one or more analytes) of the sample (e.g, urine).

Diagnostic system 40 may include a computing system 49, which may be configured to acquire, transmit, process, analyze, and/or store the diagnostic data from one or more sample collection devices 42 for any suitable number of patients for and/or over any suitable length of time.

Computing system 49 may include a data acquisition and transmission device 50 and an online service (or network) 58. For example, data acquisition and transmission device 50 may be a smartphone having a camera and processor and/or a reusable electronic device with a camera, processor, and/or transmitter configured to collect and/or transfer data from diagnostic sensors 46 and/or control 48.

As shown in FIG. 1, data acquisition and transmission device 50 may include a data acquisition device 52, such as a camera, a data transmitter 54, and a software application 56, such as a smartphone application, which may analyze the diagnostic data acquired by device 50.

Data acquisition and transmission device 50 may be any device suitable for acquiring, processing, analyzing, and/or transmitting data from sensor unit 44. In some embodiments data acquisition and transmission device 50 may be removably attached to sample collection device 42.

As shown in FIG. 1, online service 58 may include a processor 60, such as one or more servers running one or more software applications, to process and/or analyze data that online service 58 receives from data acquisition and transmission device 50. In some embodiments, online service 58 may be available over a network (e.g, internet or local) via a wireless and/or wired connection.

Online service 58 may include a notification system 62 for notifying the user by sending a notification to data acquisition and transmission device 50. The notification provided may be related to the diagnostic data from sensor unit 44 and may instruct the user to seek medical attention, such as seeing a physician, continue monitoring, such as using another diagnostic diaper every 6 hours (or any other suitable timeframe) for a desired period, and/or initiate steps to remedy a possible problem, such as having the patient drink more water. In some embodiments, the user may be the patient.

Embodiments according to aspects of the present disclosure may not in some cases replace traditional diagnostics, but rather may refer patients to see a physician at a proper time (e.g., by screening and/or monitoring a patient for a possible abnormal health condition, such as an infection or chronic condition). For example, data and any resulting warning signs produced by the software may direct the user to seek out a medical professional for additional medically established tests and a diagnosis.

In some cases, embodiments according to aspects of the present disclosure may differentiate between values that have negative and positive relationships with clinical measures, but may not in some cases achieve high accuracy in a reading of any specific parameter. Therefore, the values of each parameter detected may not necessarily correspond with values detected using traditional tools, in such cases the physician may decide to perform or prescribe more precise tests.

Online service 58 may include storage 64 (e.g., a database) to provide access to the diagnostic data over time. Thus, online service 38 may be able to analyze the diagnostic data over time and identify trends.

Computing system 49 may include a data packet 66, which may be passed between sample collection device 42 and data acquisition and transmission device 50, between data acquisition and transmission device 50 and online service 58, and/or between sample collection device 42 and online service 58.

Data packet 66 may include a timestamp 68, a date-stamp 70, a patient identifier 72, diagnostic data 74 (e.g., a digital image of a visual indication of the one or more analytes produced by diagnostic sensors 46), and/or any other appropriate or desirable data, any combination of which may be acquired by device 50. In some embodiments, data packet 66 may include a caregiver identifier 76.

Diagnostic system 40 may include multiple caregivers, multiple patients, multiple sample collection devices 42 (which may or may not be disposable or reusable either partially or totally), and multiple devices 50, which may all be coupled to or in communication with one or more online services 58.

An embodiment of a sample collection device may involve a cut-out in a top waterproof layer of a diaper, exposing the inner absorbent core of the diaper. Filter paper, which may change color based on concentration of various urine components, or other sensors may be placed in contact with the diaper's absorbent core. Non-absorbent material may be placed in the cut-out to provide a reference color that may help the analysis software on servers analyze the color changes of the filter paper. A camera phone or another wireless transmitter device may be used to capture the color changes of the filter paper or readings of other diagnostic sensors. An application on the device may process the photo and upload the processed photo over a local wireless network or a carrier wireless network to the online service. The application may upload the photo or just the information on urine content that the application understood from the photo, or the values acquired in another way other than by taking a picture. The application may also upload data on patient location and any other patient information the user has consented to be uploaded. The data capture device may also be specially engineered to have limited functions: photo capture of the urine analysis strip and transmission of the image, processing of the image, and transmission of the photo and/or data to an online service. The online service may receive the photo of the urine analysis sensor and/or data. If the photo was not processed on the data capture device, the software of the online service may process the photo to understand the values shown by the urine analysis strip (e.g., the one or more sensors). The software may then store the data in a database and may make a determination based on the current and historical data as to whether or not to warn the user of potential disease states and may recommend that the user see a physician to conduct clinical testing. These recommendations, if any, may be sent to the data acquisition and transmission device, which may include a smartphone application.

The data acquisition and transmission device may be the smartphone running the application that may download data and recommendations from the online service. The data acquisition and transmission device may display historical data on urine content and potential disease states in the form of charts and also display potential recommendations from the online service to see specialist physicians.

In one embodiment, the application running on the smartphone (i.e., an iOS-native application running on an iPhone) may be used by the caregiver to take a photo of the filter paper embedded in the diaper. The application may then upload the photo to the online service. Software running on the servers of the online service may process the photo, normalizing the colors of the filter squares using the "absolute white" reference color in the photo. The filter paper pieces may be squares (or other suitable shapes) and algorithms for detecting squares (or the other suitable shapes) are well-known in the art of computer vision, as are algorithms for color correction. An embodiment may include one or more pieces or portions of color reference material, because even though the filter paper squares can be arranged compactly, shadows from the caregiver may fall randomly, which may change the apparent color of filter paper squares.

If data acquisition is photographic, transparent tape may be placed over the filter paper or sensors and/or the reference color material. The transparent tape may be flexible enough not to break during patient movement. A reusable electronic device that is clipped onto the diaper above the filter paper pads or sensors may be an alternative way of data acquisition. The device may contain a camera or a set of current sensors that may plug into the sensors in the diaper to detect the diaper sensor values. The electronic device may communicate with the online service directly if it is enabled for example with a 3G wireless cellular chip, or it may interact with the online service via a local network with "Wi-Fi" (using an 802.11b, 802.11g, or 802.11n chip), or it may interact with the online service through the smartphone by communicating with the smartphone over the Bluetooth protocol or via Wi-Fi, or any other ways suitable for communicating with the online service. Severs may be set up to receive data from the diapers. Servers may be purchased or rented, and may be accessible via the internet. A database may be included to store the data and it may only be accessible by software running on the servers in order to maintain privacy.

FIG. 2 shows an embodiment of a sample collection device, generally indicated at 78, according to aspects of the present disclosure. As shown, sample collection device 78 is a diaper, which may be disposable or reusable either partially or totally. Diaper 78 may include a top layer 80 coupled to an absorbent core 82 (see FIG. 3), and may include a cut-out 84 in a top layer 80, which may expose absorbent core 82 of diaper 78. In some embodiments, top layer 80 may be a waterproof outer layer.

In other embodiments, diaper 78 may include a pocket or any other suitable structure, apparatus, or mechanism for accessing absorbent core 82.

As shown in FIG. 2, a diagnostic test, generally indicated at 86, may be coupled to, or included in diaper 78. For example, diagnostic test 86 may be disposed in cut-out 84, and transparent tape 88 may be disposed over diagnostic test 86 and a portion of waterproof layer 80 to seal cut-out 84.

Transparent tape 88 may be transparent waterproof film, such as OPSITE® FLEXIFIX® Transparent Film, disposed over diagnostic test 86 to provide a sufficient seal and/or to allow diagnostic test 86 to be properly viewed, which may allow the user to easily access the diagnostic data associated with the sample produced by patient P without removing diaper 78 from patient P.

FIG. 3 is a partially exploded cross-sectional view of a portion of diaper 78. As shown, diaper 78 may include a permeable bottom layer 89, absorbent core 82, and top layer 80 which may include one or more layers and may be waterproof. Bottom layer 89 may be in contact with a crotch region of the patient when diaper 78 is being worn by the patient. The sample produced by the patient may contact bottom layer 89, travel through absorbent layer 82, and contact diagnostic test 86.

Diagnostic test 86 may include an alignment frame 90, a control or reference material 92, a machine-readable code 94, and a set of one or more sensors (e.g., sensors 96a-l) disposed in a grid of reservoirs. As shown in FIG. 3, the grid of reservoirs may be formed in reference material 92. Reference material 92 may be made of a resin or other suitable hydrophobic material. One or more sensors 96 and the respective reservoirs may extend from a top surface 92a of reference material 92 to a bottom surface 92b of reference material 92.

One or more sensors 96a-l disposed in respective one or more reservoirs having perimeters made of hydrophobic material may reduce a bleeding effect of reagents in one or more sensors 96a-l, which may make reactions easier to detect by automated reading software (e.g., software application 56 and/or software running on the server of online service 58—see FIG. 1) of the computing system.

As shown in this embodiment, one or more sensors 96a-l are each square-shaped and sit in a lattice of square-shaped cut-outs (or reservoirs) formed in reference material 92. In other embodiments, one or more sensors 96a-l and/or the respective reservoirs may have other suitable shapes, such as circular or triangular shapes.

Figure 10:
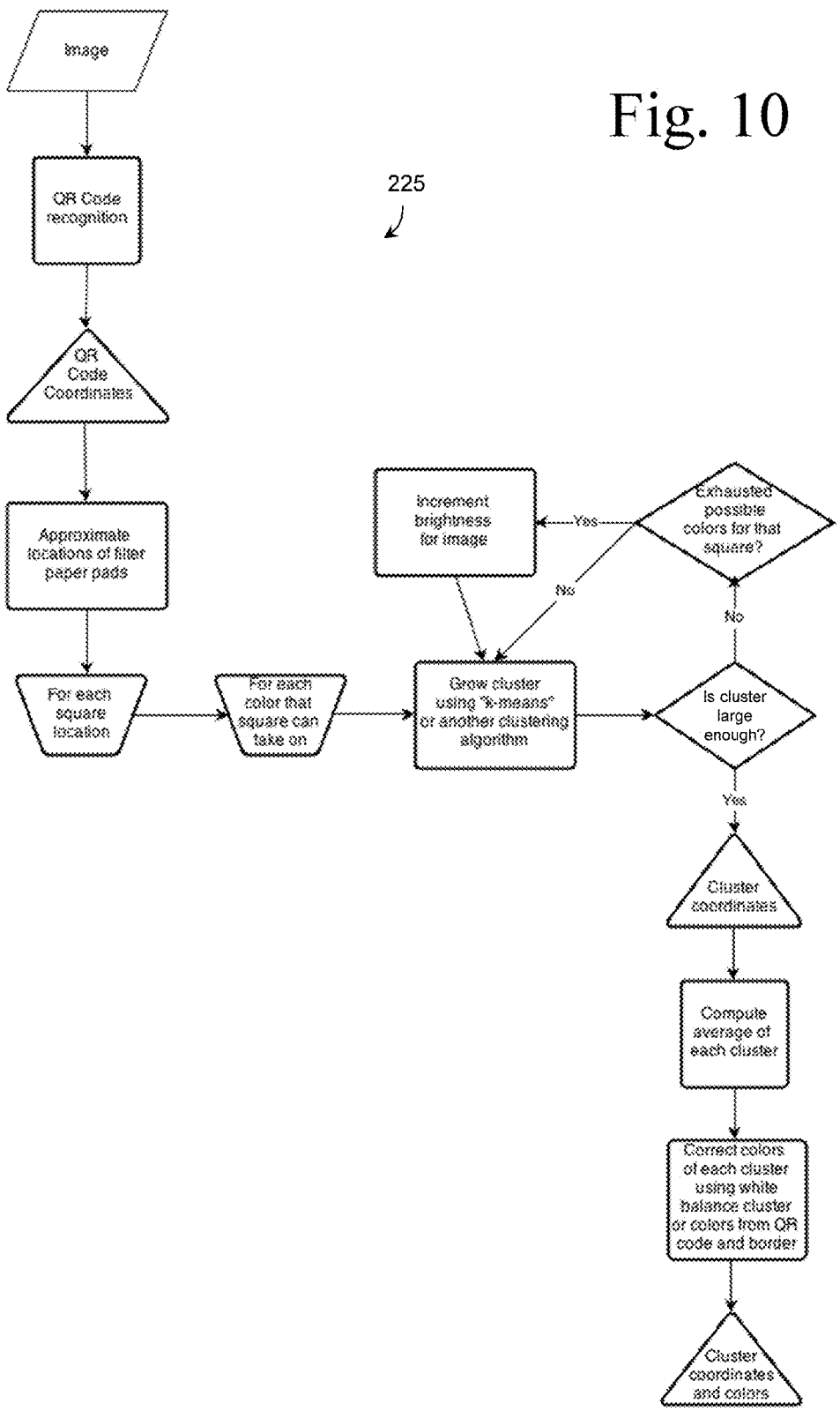
FIG. 10 is a flow-chart depicting another embodiment of an image analysis algorithm, according to aspects of the present disclosure.

An example material of the lattice in which sensors 96a-l (e.g., reagent impregnated pads) sit is 3M #9781 Single Coated Foam Tape. The lattice may prevent the pads from moving, and may prevent a dye "bleeding" effect that otherwise might produce a non-square shape, which may confuse the software algorithm. However, the software algorithm can be configured to detect the squares even if the squares have moved (e.g., relative to reference material 92), and/or configured to allow for some bleeding effect. An example of an algorithm that can successfully determine changed colors of pads even if chemical reactions result in bleeding of color onto adjacent materials is shown in FIG. 10. In FIG. 3, alignment frame 90 is shown to be a rectilinear frame surrounding the set of one or more sensors 96a-l, machine-readable code 94 is shown positioned approximately in the center of alignment frame 90, reference material 92 is shown surrounding each of sensors 96a-l, and one or more sensors 96a-l are shown substantially surrounding machine-readable code 94 and are positioned between machine-readable code 94 and alignment frame 90.

In other embodiments, alignment frame 90 may form another suitable outline for diagnostic test 86. For example, the alignment frame may be circularly shaped.

One or more sensors 96a-l may be configured to produce a visual indication of one or more analytes contained in the sample produced by the patient in a first interval of time (e.g., a portion of bodily waste produced by the patient). For example, one or more sensors 96a-l may be in fluid communication with absorbent core 82, and each of sensors 96a-l may include one or more reagents configured to react with one or more specific analytes which may be contained in the sample to produce the visual indication (e.g., a change in color or color intensity of one or more sensors 96a-l) that communicates an at least quasi-quantitative, semi-quantitative, and/or qualitative indication of a presence of, or an amount of the one or more analytes contained in the sample.

For example, sensor 96a may be configured to change from a first preselected color (shown) to a second preselected color (or a different color intensity) to indicate a presence of a first analyte in the sample (e.g., ketones in a portion of urine). Sensor 96b may be configured to change from a third predetermined color (shown) to a fourth predetermined color (or color intensity) to indicate an approximate level or concentration of a second analyte in the sample (e.g., a specific gravity of the portion of urine). Sensors 96c-l may be configured to similarly detect and provide a visual indication of the first and/or second analyte and/or any other suitable preselected analyte, such as glucose, bilirubin, blood, pH, protein, urobilinogen, nitrite, leukocytes, and/or creatinine, among others.

Chemistries and methods of detecting analytes by producing a visual indication are well known in the art. For example, see U.S. Pat. Nos. 5,516,700; 4,318,709 4,147,514; and 3,146,070 which are all hereby incorporated by reference.

Alignment frame 90 may be configured to assist the user in aligning a view finder of the camera with diagnostic test 78. For example, the computing system may instruct the user to orientate the camera so that alignment frame 90 is substantially aligned with a perimeter of an image shown in the view finder of the camera, which may ensure that all of visual indications of one or more sensors 96a-l and/or machine-readable code 94 will be captured by the camera (e.g., in a digital image or photo).

Reference material 92 may be configured to help the computing system correct an image for lighting conditions. For example, reference material 92 may be true white in color. The computing system may be preprogrammed to determine a color-correction (e.g., if a shadow falls on a portion of diagnostic test 86) based on a comparison of a color of reference material 92 in the image to true white.

As shown in FIG. 3, reference material 92 surrounds each of sensors 96, which may assist the computing system in color-correcting only a portion of the image on which the shadow may fall. For example, the shadow may fall on sensor 96g, but not on sensor 96f, in which case reference material 92 distal sensor 96f and surrounding a portion of sensor 96g may appear darker than reference material 92 proximal sensor 96f. The computing system may be configured to identify such a gradient in apparent color of reference material 92 and may color-correct a region of the image corresponding to a darker region but not a lighter region (e.g., may color-correct a region of the image corresponding to sensor 96g, and not color-correct, or color-correct less, a region of the image corresponding to sensor 96f.)

The colors of machine-readable code 94 may help an algorithm of the computing system color correct the image of diagnostic test 86. For example, machine-readable code 94 may include a true black color and a true white color. The computing system may be configured to associate a darker region of machine-readable code 94 with true black, to associate a lighter region of machine readable code 94 with true white, and to color correct the image accordingly.

In some embodiments, white or black squares or other colors and/or shapes, or combinations thereof, of machine-readable code 94 can be used for color correction by the algorithm of the computing system. For example, machine-readable code 94 may be a QR code printed in different colors (e.g., printed in blue with red "control" squares at the corners). These colors, as well as the color of the panel's border (e.g., alignment frame 90) can also be used for color correction. For example, the color of alignment frame 90 may be printed with (only) a little deviation, if any, from print lot to print lot, and the color of alignment frame 90 may be used for color correction by the algorithm.

As shown in FIG. 3, Machine-readable code 94 is a QR code. However, machine-readable code 94 may be any suitable code configured to be read by the computing system. For example, machine-readable code 94 may include any suitable barcode, such as a linear barcode, such as a codabar, a "code 25" (non-interleaved 2 of 5, or interleaved 2 of 5), a "code 11", a "code 39", a "code 93", a "code 128", a "code 128A", a "code 128B", a "code 128C", a CPC Binary, a "DUN 12", a "EAN 2", a "EAN 5", a "EAN 8", a UPC, or any other suitable linear barcode.

In other embodiments, machine readable code 94 may include any suitable 2D or matrix barcode, such as a 3-DI, an ArrayTag, an AugTag, an Aztec Code, a Data Matrix, a High Capacity Color Barcode, a MaxiCode, a PDF417, a ShotCode, or SPARQCode.

Machine-readable code 94 may include manufacturing batch information, such as a production date, a predetermined expiration date, a version number, and a production batch number of diagnostic test 86.

In some embodiments, machine-readable code 94 may be printed or disposed on reference material 92. In other embodiments, machine-readable code 94 may be printed or disposed on transparent tape 88.

Machine-readable code 94 may include instructions that enable the computing system to automatically scan diagnostic test 86 of diaper 78 (e.g., so that the user does not have to press a button). For example, machine-readable code 94 may instruct an application running on the computing system to automatically check each frame acquired by the camera to determine if the frame is in focus, and then analyze and upload to the server only that frame or a set of frames immediately before and immediately after the frame that is deemed to be in-focus.

Machine-readable code 94 may include instructions that direct the computing system (e.g., a software application running on the computing system) to automatically perform at least one task related to an acquisition and/or analysis of the diagnostic data. For example, machine-readable code 94 may include instructions that direct the computing system to take one or more digital images of diagnostic test 86; to select a focused digital image of the at least quasi-quantitative, semi-quantitative, and/or qualitative indication of one or more sensors 96a-l; to identify a format of diagnostic test 86; to determine whether diagnostic test 86 has expired past the predetermined expiration date; and to determine an authenticity of diagnostic test 86.

Identifying a format of diagnostic test 86 may involve identifying a format, layout, and/or version of reagents included in one or more sensors 96a-l, which may assist the computing system in analyzing the visual indication. For example, machine-readable code 94 may indicate relative positions of one or more sensors 96a-l, the specific reagents included in one or more sensors 96a-l, the specific one or more analytes that one or more sensors 96a-l are configured to detect, a layout of the grid of reservoirs in which one or more sensors 96a-l are disposed, and/or one or more abnormal health conditions (e.g., one or more diseases) that may be associated with the specific one or more analytes.

For example, machine-readable code 94 may indicate that one or more of sensors 96a-l include reagents and concentrations of chemical compositions corresponding to traditional urinalysis testing reagents. For example, the sensors may be configured to detect each of the below when impregnated with the following concentrations of chemical compositions:

Urobilinogen detected with a sensor impregnated with 4-Metoxybenzenodiazonium 0.025 mg and Citric acid 0.3 mg Glucose detected with a sensor impregnated with Glucose oxidase 0.0451 units, Peroxidase 0.0186 units, and Potassium iodide 0.1 mg Ketones detected with a sensor impregnated with Sodium nitroprusside 0.2 mg and Magnesium sulfate 2.465 mg Bilirubin detected with a sensor impregnated with 2,4-Dichlorophenyldiazonium 0.03 mg and Oxalic acid 0.3 mg Proteins detected with a sensor impregnated with Tetrabromophenol blue 0.003 mg, Citric acid 1.1 mg, and Trisodium citrate 0.46 mg Nitrite detected with a sensor impregnated with p-Arsanilic acid 0.05 mg and N-(naphthyl)-ethylenediamine 0.006 mg pH detected with a sensor impregnated with Methyl red 0.0004 mg and Bromothymol blue 0.005 mg Blood detected with a sensor impregnated with Hydroperoxide 0.04 mg and 3,3',5,5'-Tetramethylbenzidine 0.037 mg Specific gravity detected with a sensor impregnated with Bromothymol blue 0.012 mg and Polyelectrolyte 0.12 mg Leukocytes detected with a sensor impregnated with Pyrazol amino acid ester 0.01 mg, and Diazonium salt 0.007 mg It will be appreciated that a set of sensors may be used to detect each or all of, or a subset of, the above identifiers and/or the sensors may include other tests, reagents, and/or concentrations of reagents for detecting the above or other identifiers being detected by producing any response desired when exposed to the sample being analyzed. Some or all of the sensors may include the same reagents to detect the same identifier in order to create a redundancy to help ensure the accuracy of the results detected.

Diaper 78 may include any suitable configuration of diaper layers and components for collecting a sample, such as urine, sensing sample content, providing for patient comfort, providing for convenience of use and/or viewing the diagnostic data. For instance, the sensors may be fixedly attached to a filter paper pad and/or the transparent film and disposed in the cut-out. Additionally, a privacy cover layer (not shown) may be removably attached and configured to diaper 78 so that diaper 78 has an appearance of a regular diaper, which may be desirable for maintaining confidentiality.

FIG. 4 shows a top plan view of an embodiment of a diagnostic test 86. In the embodiment shown, alignment frame 90 forms a perimeter around sensors 96*a-l*, and sensors 96*a-l* are substantially evenly disposed around machine-readable code 94. Disposing sensors 96*a-l* substantially evenly around machine-readable code 94, may promote a likelihood that all of the visual indications of sensors 96*a-l* will be captured in the digital image. In contrast, disposing all of sensors 96*a-l* to one side of machine-readable code 94 may increase a chance that the user might position the camera in such a way as to leave a visual indication of one of sensors 96*a-l* out of the digital image.

In some embodiments, alignment frame 90 may have a different color than top surface 92*a* of the reference material.

FIG. 5 shows a bottom plan view of diagnostic test 86. As shown in FIGS. 4 and 5, sensors 96*a-l* and the respective reservoirs extend through reference material 92. In other words, sensors 96*a-l* and the respective reservoirs extend from and through top surface 92*a* (see FIG. 4) to and through bottom surface 92*b* (see FIG. 5).

FIG. 6 shows a top plan view of another embodiment of a diagnostic test, generally indicated at 98. Diagnostic test 98 may include one or more sensors (e.g., sensors 100*a-k*), such as filter paper pads of square or another suitable shape, impregnated with chemical reagents that produce a colorimetric response when exposed to a sample, such as urine, produced by the patient. Reagents may include sodium nitroprusside and magnesium sulfate, such as for reacting with ketones and urine, hydroperoxide and 3,3',5,5'-Tetramethylbenzidine for reacting with blood in urine, and/or any other chemical reagents that are or are not used on traditional urinalysis strips, such as the 11 PARAMETERS ULTRA® Test Strips from BTNX inc. or Siemens MULTISTIX®, and disposed in the cut-out 84 (see FIG. 3) so as to be sufficiently exposed to a sample, such as urine, produced by the patient. As shown, sensors 100*a-k* may be one or more colored filter paper pads or any other suitable diagnostic sensor or combination thereof, and may also include one or more controls 102, which may include one or more non-absorbent reference color materials as shown or any other suitable control.

Sensors 100*a-k* and controls 102 may be disposed on an absorbent sheet 104. Absorbent sheet 104 may be coupled to absorbent core 82 (see FIG. 3) through cut-out 84. The transparent waterproof film may then be disposed on diaper 78 to seal cut-out 84 and provide visual access to sensors 100*a-k* and controls 102.

As shown in FIG. 6, controls 102 may be two rectangular pieces of white color-reference material. Each of controls 102 may be used to correct the color of neighboring filter squares (e.g., sensors 100*a-k*). After detection and correction, the color of the filter paper squares may be matched to the closest color in a table mapping colors to values of each parameter and the filter paper squares may be assigned corresponding appropriate values.

The values for each parameter, along with a timestamp, and patient identifier may be stored in the online service, which may include a database. The software may then compare the values for each parameter over time (for example: over three days, seven days, and/or 30 days), looking for trends such as those that would, for example, point to the patient undergoing ketoacidosis. The software may also look for parameter values that are too high and may thus immediately point to a problem. The software may then send a message to the application running on the smartphone if a trend in the data implies that the caregiver needs to take an action such as give fluids to the patient, perform additional monitoring, and/or seek a diagnosis from a physician.

For example, diabetic ketoacidosis is a potentially life-threatening complication that may develop slowly in people with diabetes mellitus. Diabetic ketoacidosis happens predominantly in those with type 1 diabetes, but it may occur in those with type 2 diabetes under certain circumstances. Diabetic ketoacidosis results from a shortage of insulin, when the body switches to burning fatty acids and producing acidic ketone bodies that cause most of the symptoms and complications. Diabetic ketoacidosis may be the first symptom of previously undiagnosed diabetes. For example, as ketoacidosis develops slowly, if the online service detects a trend of rising ketone levels over a course of 30 days, but the level has not yet reached 40 mg/dL, it may warn the caregiver that the patient wearing the diagnostic diapers should be seen by a physician to check for other signs of diabetes, such as high blood glucose. If the online service detects, for example, three days during a seven day period in which ketone levels are at or higher than 40 mg/dL, but below 80 mg/dL, the online service may tell the caregiver that the patient in diapers needs to see a physician immediately. If ketone levels reach 80 mg/dL, the online service may ask the caregiver to put a new diaper on the patient in six hours. If the next diaper reading shows level of ketones to be above 80 mg/dL, the caregiver may be instructed to contact the patient's physician immediately, as well as give liquids to the patient to prevent dehydration.

In some embodiments, sensors 100*a-k* and controls 102 may be coupled to a sheet and inserted into or removably inserted into the diaper, so as to provide a diagnostic test that may be used with any suitable diaper.

In some embodiments, for each pad of filter paper that denotes a parameter and touches the absorbent core, a pad of the same filter paper can be placed in a way so that the pad of the same filter paper does not touch the absorbent core and thus may always provide an original (pre-wet) color control that a corresponding wet pad can be compared to.

Diaper 78 (see FIG. 2) may be a customized diaper, in which, for example sensors 100*a-k* (see FIG. 6) and controls 102 may be coupled or releasably coupled to the diaper in any suitable position, such as on or near an outside, inside, and/or middle of the diaper, and/or through one or more layers of the diaper, for any suitable diagnostic test. For example, a diagnostic test using a sweat sample may be placed on an inside side portion of the diaper, in order to collect diagnostic data from sweat but not urine or feces, and/or a diagnostic test using a feces sample may be placed on an inside rear portion of the diaper, and/or a diagnostic test using an environmental sample may be placed on an outside surface of the diaper. The diagnostic test may also include a sticker with one or more diagnostic sticker(s) and control(s), which may be releasably adhered to or fixedly adhered to an inside portion of a diaper, such as a standard off-the-shelf diaper.

In some embodiments, after a diaper becomes wet, the user may add a solution of or more aptamers attached to a colloidal material to the diaper and then observe a reaction of one of the filter paper pads with urine and the aptamer solution. The reaction may produce a colorimetric indication that can then be automatically read by the application running on the computing system (e.g., the application running on the smartphone and/or the application running on the server).

In some embodiments, diaper 78 (see FIG. 2) may include diabetes diagnostic filter paper squares and non-absorbent color reference material coupled to the absorbent core; urinary tract infection and renal disease diagnostic filter papers and non-absorbent color reference material coupled to the absorbent core; diabetes, urinary tract infection, and renal disease diagnostic filter papers and two strips of non-absorbent color reference material coupled to the absorbent core.

Sample collection device 42 (see FIG. 1) may include one or more diagnostics capable of providing any suitable data for monitoring health. For example, sample collection device may include sensors (e.g., filter paper impregnated with one or more reagents) to detect levels of glucose, bilirubin, ketone, specific gravity, blood, pH, protein, urobilinogen, nitrite, leukocytes, creatinine, and other desirable factor which may be contained in the urine or other sample produced by the subject.

Some embodiments of the present teachings may include a diaper that may be used to acquire data about diabetes-related urine content (glucose, ketones, and other parameters such as ascorbic acid that may be used to deem the values of glucose and ketones to be unreliable); to acquire data about urinary tract infections (leukocytes, blood, pH level, and any additional parameters that may be used to deem the values of the first three sensors to be unreliable); and/or to acquire data about precursors of or developed renal diseases (such as creatinine and albumin, as well as any parameters that may be used to deem values of creatinine and albumin to be unreliable).

While each diaper may contain additional sensors for parameters that may immediately be used to determine whether the main parameters' values should not be relied upon, these values may not be used on their own to rule out false positives or perform other statistical calculations. Statistical calculations may be performed on data aggregated over sufficient time such that statistically meaningful conclusions may be reached.

An embodiment of sample collection device 42 may include a diagnostic for electrolyte disorders. For example, changes in intra- and extra-cellular potassium levels may modify the electrophysiologic properties of the resting membrane potential in cardiac cells and subsequently influence the generation and conduction of impulses throughout the heart. Extracellular potassium homeostasis may be regulated mainly by the kidneys and homeostasis may be achieved when kidney excretion matches oral intake. Serum hypokalimia may be associated with increased risk of ventricular arrhythmia among patients admitted to a hospital with myocardial infarction. Detecting high concentrations of potassium in urine in a child, before intravenous potassium replacement therapy or potentially bowel-damaging oral therapy may help delay or prevent long term changes to the heart muscle's ability to generate and conduct electric impulses. In adults, detecting hypokalimia may help initiate potassium replacement therapy and initiate monitoring for ventricular arrhythmia.

Diseases and diagnostic data from associated diagnostics mentioned in the present disclosure are exemplary and should not be viewed as limiting. One or more diagnostic tests may be used on the diaper.

FIG. 7 depicts an embodiment of diagnostic system 40 (see FIG. 1), generally indicated at 142, in which data may be acquired from one or more diagnostic diapers 78, which may be worn by one or more patients, and may include one or more smartphones S configured to acquire the diagnostic data from one or more diagnostic diapers 78 and upload the diagnostic data and/or receive notifications from online service 58. As shown, online service 58 may be provided in a cloud environment and may include database 64 and servers 60 with software. Diagnostic system 142 may be configured to analyze diagnostic data from a multitude of patients over multiple time frames and may store the diagnostic data for future analysis, which may provide for a way to conduct epidemiological analysis. Furthermore, anything that happens (e.g., analysis) on device 50 (see FIG. 1), in this case smartphone S, could also happen in online service 58 and vice-versa.

Moreover, with every measurement, the accuracy of diagnostic system 142 may improve. For example, urine analysis strips may be characterized as inexact, as urine analysis strips can be confounded by diet and/or time displacement from a meal, thus possibly producing false positives and/or false negatives. Diagnostic system 142 may reduce false positives and/or false negatives by aggregating multiple measurements for a patient and/or similar patients over time. Examples of similar patients may include children from a family unit who consume a similar diet, patients who are identified by the online service as being similar, and/or patients who are identified by a caregiver as being similar.

Figure 8G:
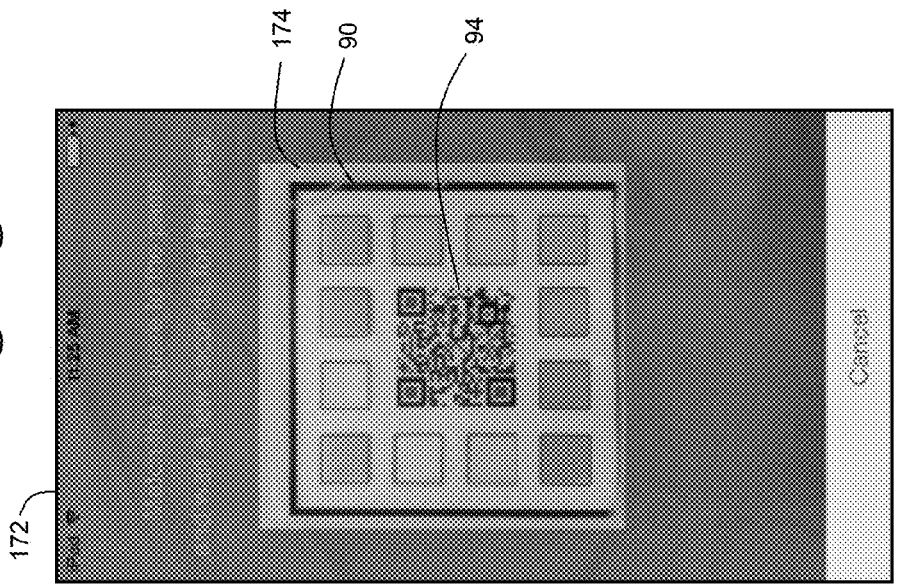
FIGS. 8*a-n* are screenshots depicting an embodiment of a software application of the diagnostic system of FIG. 1.
Figure 8F:
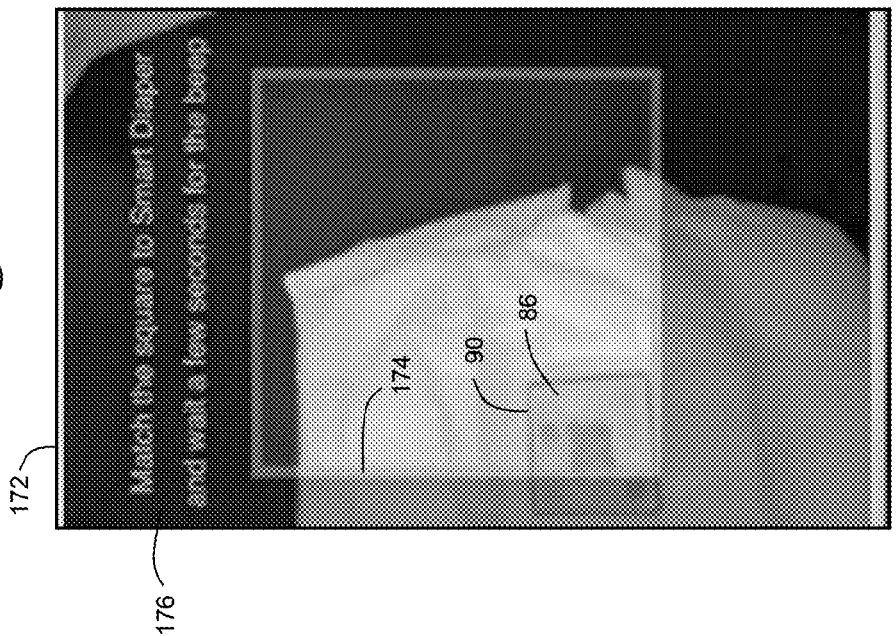
Figure 8M:
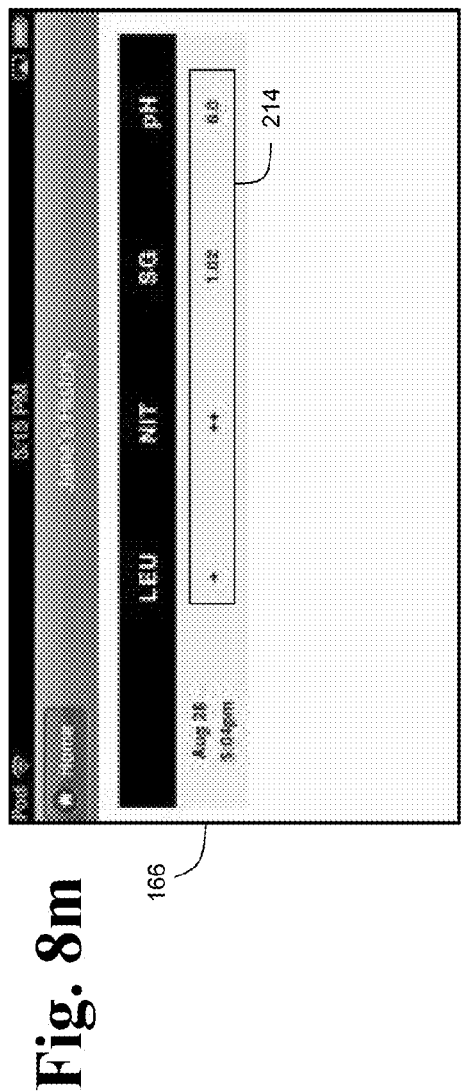
Figure 8N:
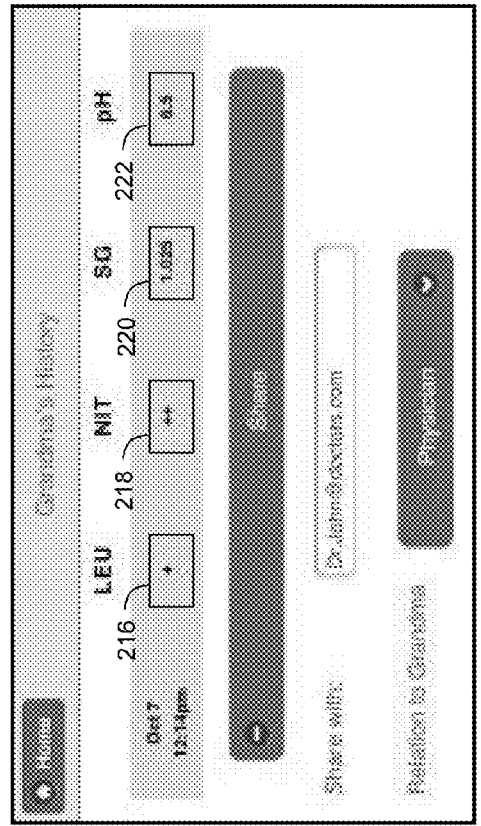

FIGS. 8*a-n* are screenshots depicting an exemplary software application 56 (see FIG. 1). Software application 56 may be described as an auto-detect software application for a smartphone.

FIG. 8*a* shows a logon screen 150 through which the user may logon to software application 56 (see FIG. 1) and/or online service 58.

FIG. 8*b* shows a registration screen 152 through which the user may register an account for software application 56 and/or online service 58.

FIG. 8c shows an add-patient screen 154 through which the user may add a patient, such as one or more children of the user. Add-patient screen 154 may include a name field 156 for identifying the patient added, a born-on field 158 for identifying an age of the patient, a diaper size field 160 for identifying a diaper size that the patient currently wears, and a gender field 162 for identifying a gender of the patient.

FIG. 8d shows a summary page 164, which may display all of the patients for whom the user is collecting diagnostic data. As shown, the user is currently only collecting data for one patient, who is identified here as Jane.

By selecting a patient in summary page 164, the software program may be configured to display a history page 166 for the patient selected, in this case Jane, as shown in FIG. 8e. History page 166 may include an indicator field 168, which indicates abnormal health conditions for which the user may desire to screen and/or monitor the patient, in this case urinary tract infection (UTI) and hydration (or dehydration).

History page 166 may include a monitor health button 170 (or touch screen location), which when selected may initiate an automatic reading (or scanning of a diagnostic test, such as diagnostic test 86 coupled to diaper 78—see FIG. 2).

By selecting monitor health button 170 in FIG. 8e, the software application may be configured to turn on the camera of the smartphone and display the frame of the camera on a find-diagnostic test screen 172 (see FIG. 8f), which may include an alignment frame 174 and instructions 176. Instructions 176 may direct the user to match alignment frame 174 with alignment frame 90 of diagnostic test 86 and wait for a beep (or other suitable signal).

FIG. 8g shows an embodiment of alignment frame 174 of screen 172 substantially matched with alignment frame 90. The software application may be configured to identify and/or read the instructions of machine-readable code 94 when the alignment frame 174 and alignment frame 90 are substantially matched and to emit a signal, such as an audible indication (e.g., the beep), to the user when the software application has successfully acquired the visual indication of the one or more sensors.

After the software application has successfully acquired a suitable digital image of the visual indication of the one or more sensors, the software application may be configured to transition back to history screen 166, and display a subscreen 177, as shown in FIG. 8h, and/or a subscreen 178, as shown in FIG. 8i, to indicate that the computing system (e.g., the smartphone and/or the online service) is analyzing the digital image to produce a diagnostic data point (or a health monitoring data point, or a health screening data point) based on the visual indication of the one or more sensors.

If the diagnostic data indicates that the one or more analytes of the bodily waste produced by the patient is associated with an abnormal health condition, then the software application may display a notification subscreen 180 on history screen 166, as shown in FIG. 8j.

FIG. 8k shows history screen 166 after multiple data points over a period of time have been collected for the subject (i.e., Jane). For example, the user may have disposed a first diaper on the subject for collecting a first portion of bodily waste produced by the subject in a first interval of time. A first diagnostic test may be coupled to (or included in) the first diaper. The first diagnostic test may have a first set of one or more sensors configured to produce a first visual indication of one or more analytes contained in the first portion of bodily waste. A first machine-readable code may be disposed near the first set of one or more sensors. The computing system may be configured to visually read the first machine-readable code to allow an application running on the computing system to perform at least one task related to a production of a first health monitoring data point 182 based on the first visual indication.

The user may have then disposed a second diaper on the subject for collecting a second portion of bodily waste produced by the subject in a second interval of time. A second diagnostic test may be coupled to (or included in) the second diaper. The second diagnostic test may have a second set of one or more sensors configured to produce a second visual indication of one or more analytes contained in the second portion of bodily waste. A second machine-readable code may be disposed near the second set of one or more sensors. The computing system may be configured to visually read the second machine-readable code to allow the application running on the computing system to perform at least one task related to a production of a second health monitoring data point 184 based on the second visual indication.

The above can be repeated to generate a third health monitoring point 186 through an N health monitoring point. The above can be repeated as many times as needed as desired to collect and analyze sufficient data over time.

In some embodiments, the first, second, and third machine-readable codes may be configured to prevent the computing system from entering a specific data point more than once. For example, the user may inadvertently scan a specific diagnostic test more than one time, in which case the computing system may be configured to recognize the inadvertent mistake by recognizing a repeat machine-readable code.

As shown in FIG. 8k, history screen 166 indicates to the user that first data point 182 produced at a first instance in time 188 (e.g., substantially immediately following the first interval of time) is not associated with a UTI (e.g., by displaying a green dot 190 in a UTI column) and is associated with dehydration (e.g., by displaying a red dot 192 in a hydration column); that second data point 184 produced at a second instance in time 194 (e.g., substantially immediately following the second interval of time) is associated with a UTI (e.g., by displaying a red dot 196 in the UTI column) and is associated with dehydration (e.g., by displaying a red dot 198 in the hydration column); and that third data point 186 produced at a third instance in time 200 (e.g., substantially immediately following the third interval of time) is associated with a UTI (e.g., by displaying a red dot 202 in the UTI column) and is associated with dehydration (e.g., by displaying a red dot 204 in the hydration column).

Longitudinal analysis, such as that described above, may improve health monitoring/screening in diagnostic systems, according to the present disclosure. For example, when attempting to detect a condition of dehydration (or poor hydration), a single reading (e.g., data point) of specific gravity at or higher than 1.02 may not be a good signal of whether there is dehydration, but more than X of the last Y daily readings of specific gravity at or higher than 1.02 may indicate mild dehydration.

In another embodiment, a detection of a possible diabetic ketoacidosis condition may be performed by seeing if more than X of the last Y daily readings (e.g., data points) show that the urine of the subject is positive for ketones and/or glucose. A single reading may not be determinative, so multiple readings may be needed.

In some embodiments, the computing system may be configured to send a notification, such as notification 206 (see FIG. 8k), to the user if more than one of the data points are associated with an abnormal health condition (e.g., if one or more analytes or levels thereof are associated with the abnormal health condition and/or fall outside a predetermined or predefined range). As shown in FIG. 8k, notification 206 may include an indication of a likelihood of the abnormal health condition in the subject and an indication to contact a medical professional.

As shown in FIG. 8*l*, history screen 166 may include a share-with field 208 configured to allow the user to input an email address (or other suitable identifier) of a third party to whom the user desires to send/share the data points (and/or other desirable data, such as the notification and/or the digital images of the visual indications of the one or more sensors). The user may select a relationship of the third party to the patient in a field 210. For example, field 210 may be a pull down menu that allows the user to identify the third party as a medical provider (i.e., doctor), friend, parent, relative (i.e, grandmother), care provider (i.e., day care or nanny), researcher, etc. The user may send any or all the data points (and/or other suitable data) selected as desired to the third party by activating a share button 212.

The software application may be configured to display one or more at least quasi-quantitative and/or qualitative indications of one or more analytes contained in the bodily waste of the subject. For example, FIG. 8*m* shows history screen 166 displaying a data point 214 including an indication that the bodily waste of the subject is positive for leukocytes, very positive for nitrites (which may indicate that the subject has a UTI), a specific gravity of 1.02, and a pH of 6.0.

The software application may allow the user to screen and/or monitor the health of more than one patient. For example, the user may add a grandmother of the user in screen 154 (see FIG. 8*c*). A profile corresponding to the grandmother may then appear on screen 164 (see FIG. 8*d*). The user may select the profile of the grandmother, and the computing system may acquire and analyze a visual indication of one or more sensors configured to detect one or more analytes in bodily waste produced by the grandmother, and to produce a diagnostic data point based on the visual indication. As shown in FIG. 8*n*, an exemplary diagnostic data point for the grandmother may include a qualitative indication 216 of a first analyte (e.g., that the bodily waste is positive for leukocytes, or very positive for leukocytes), a quasi-quantitative indication 218 of a second analyte (e.g., that the bodily waste is very positive for nitrites), a quantitative indication 220 of a concentration of a third analyte (e.g., that the bodily waste has a specific gravity of 1.025), and a quantitative indication 222 of a fourth analyte (e.g., that the bodily waste has a pH of 6.5).

In some embodiments, the smartphone software application may provide a way to manage patients. For example, the patients may be children and the user may be a parent of the children. The application may provide a way of selecting a date, dating and/or time-stamping, and/or a way of selecting a diagnostic (or screening and/or monitoring test) to be performed, such as a kidney, hydration, and/or infection diagnostic. The application may provide a way of acquiring an image of the one or more sensors and a control portion if included in the diagnostic test. The application may process, analyze, transmit, and/or upload the image and/or any related data to the online service 58 or any other desirable location. The application may also include a way of indicating successful data acquisition and/or transmission of data and, as previously discussed, may further include ways of notifying the user of a potential illness and/or receiving the notification from the online service.

Figure 9:
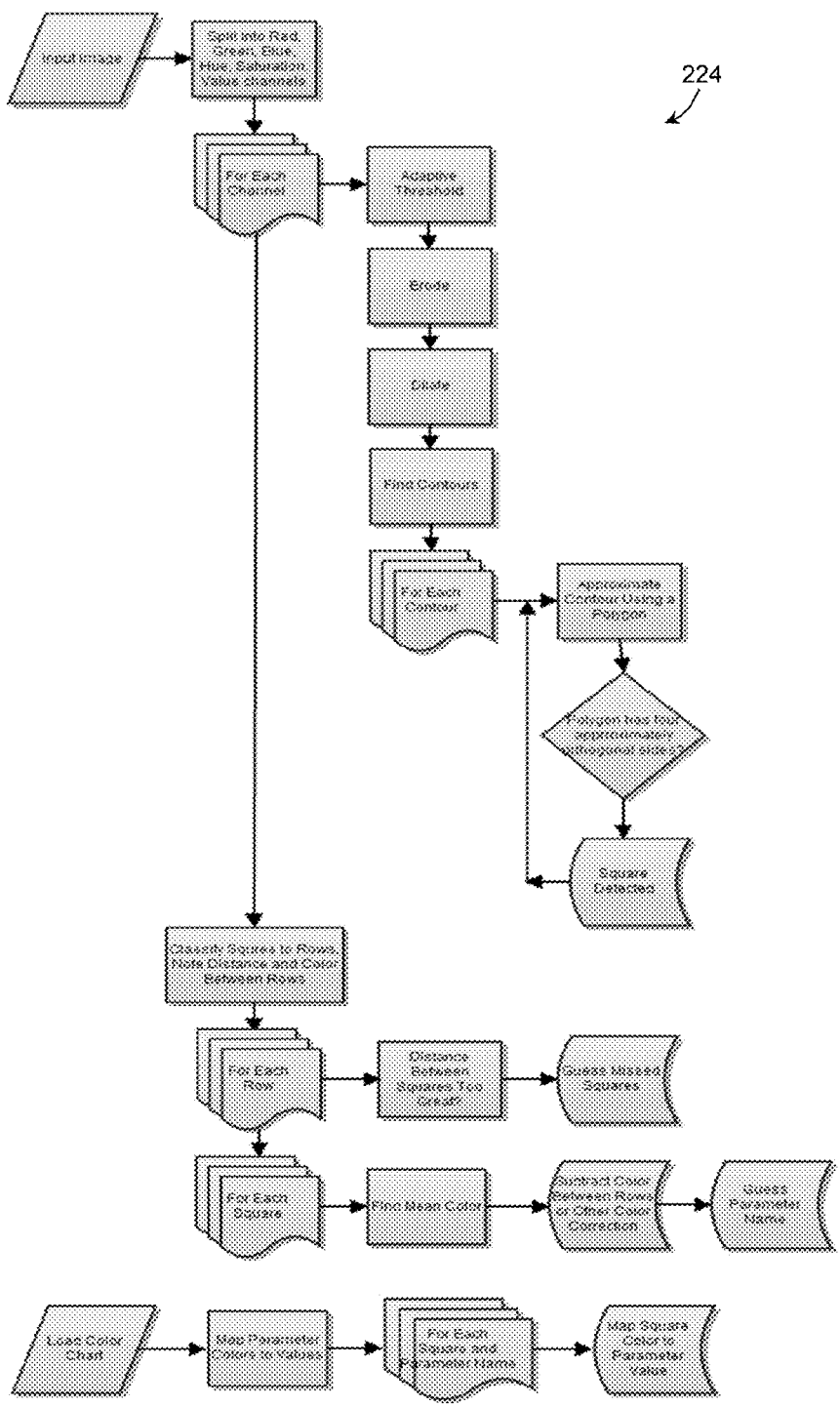
FIG. 9 is a flow-chart depicting an algorithm for recognition of diagnostic data, according to aspects of the present disclosure.

FIG. 9 is a flow-chart depicting an algorithm, generally indicated at 224, for recognition of diagnostic data from an input image, such as a digital image of the visual indication of the one or more sensors. Algorithm 224 may be included in or configured to the software application of FIG. 8 and/or software running on the online service. As depicted, the input image (e.g., of sensors 96*a*-*l* and control 92—see FIG. 3) may be split into red, green, blue, hue, and/or saturation valve channels. One or more channels may then be analyzed to recognize one or more filter paper sensors and/or to assign a parameter value to the one or more filter paper sensors. As shown, each channel may include analysis of an adaptive threshold, an erode function, a dilate function, and/or a find contours function. For each contour, the analysis may include an approximate contour function which may use a polygon (or other suitable predefined shape) and a determination as to whether or not the polygon has four approximately orthogonal sides in order to detect an approximate square. However, the machine-readable code may instruct the software application to use another suitable subroutine for determining whether or not the software application has correctly identified the one or more sensors. For example, if the machine-readable code identifies the format of the diagnostic test as including circle shaped sensors, the software application may alter algorithm 224 to approximate the contours using a circle.

As shown in FIG. 9, each channel may include a classification of squares into rows and a notation of distance and color between rows. For each row, analysis may include a determination as to whether or not a distance between squares may be too great, which may indicate that a guess missed the squares. For each square, analysis may include a find mean color function, which may find an average color for each square, a subtract color between rows function and/or other color correction function, and a function to guess a parameter name. Furthermore, analysis may include a color chart which may be loaded, a map parameter colors to values function, and a map square color to parameter value function, which may be applied to each square and parameter name. As previously stated, the analysis of diagnostic data may further include consideration of the control.

FIG. 10 is a flow-chart depicting an alternative image analysis algorithm, generally indicated at 225, according to aspects of the present disclosure. Algorithm 225 may be configured to receive an input image, and may be configured to recognize a QR code (e.g., machine-readable code 94 of FIG. 4, or other suitable machine-readable code) in the image, and to extract information (and/or instructions) from the QR code, such as coordinates of one or more sensors (e.g., sensors 96*a*-*l*—see FIG. 4) of an associated diagnostic test (e.g., diagnostic test 86).

Algorithm 225 may be configured to approximate locations of the one or more sensors (e.g., filter paper pads), for example, by associating the coordinates of the one or more sensors with the approximate locations of the one or more sensors in the image.

Algorithm 225 may identify the locations of the one or more sensors as square locations (e.g., the extracted information may indicate that the one or more sensors are square-shaped sensors).

Algorithm 225 may, for each square location (or other suitably shaped location) and for each color that a particular square (e.g., sensor) can take on (or change to), grow a cluster using "k-means" or any other suitable clustering algorithm.

Algorithm 225 may then determine if the cluster is large enough. For example, algorithm 225 may compare a size of the cluster to a predetermined threshold size.

If the cluster is not large enough (e.g., if the size of the cluster is less than the predetermined threshold size), then algorithm 225 may check to see whether possible colors for that square (or other determined shape) have been exhausted. If possible colors have not been exhausted, then algorithm 225 may return to growing the cluster using "k-means" or another suitable clustering algorithm. If possible colors have been exhausted, then algorithm 225 may increment a brightness for the image (e.g., increase or reduce the brightness), and may then return to growing the cluster.

If the cluster is large enough, then algorithm 225 may identify cluster coordinates for the cluster.

Algorithm 225 may compute an average of each cluster. For example, algorithm 225 may compute an average color for each cluster.

Algorithm 225 may then correct colors using a white balance cluster and/or colors from the QR code or border. For example, algorithm 225 may color-correct each average color using the white balance cluster and/or colors from the QR code or border.

Algorithm 225 may then associate the color-corrected average color of each sensor with the respective cluster coordinates. The color-corrected average colors and associated cluster coordinates may then be used by the computing system to produce diagnostic data.

Figure 11:
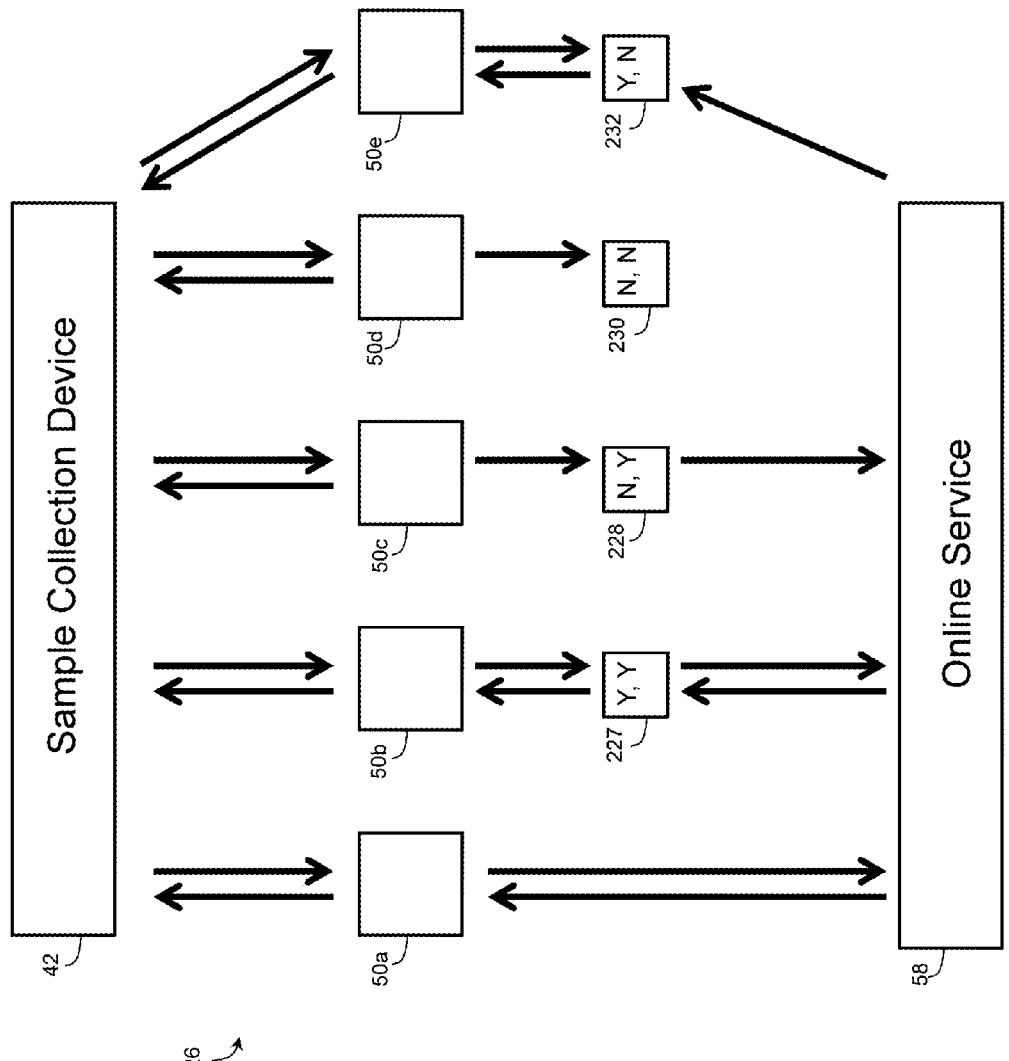
FIG. 11 depicts another illustrative embodiment of the diagnostic system of FIG. 1.

FIG. 11 depicts an embodiment of a diagnostic system, generally indicated at 226, according to aspects of the present disclosure. Diagnostic system 226 may include more than one data acquisition and transmission device 50, such as devices 50a, 50b, 50c, 50d, and/or 50e which may each acquire, transmit, and/or receive data from sample collection device 42 and/or online service 58. Devices 50b, 50c, 50d, and/or 50e may be configured to online service 58 with respective permission controls 227, 228, 230, and 232, which may be controlled by device 50a and/or online service 58 in order to block or permit devices 50b, 50c, 50d, and/or 50e from transmitting and/or receiving data from online service 58. For example, the user of device 50a may be a parent and users of devices 50b, 50c, 50d, and 50e may be other caregivers, in which case varying levels of access may be desirable. As shown, permission control 227 may be configured to permit device 50b to transmit data to and receive data from online service 58; permission control 228 may be configured to permit device 50c to transmit data to online service 58 but not to receive data from online service 58; permission control 230 may be configured to block device 50d from transmitting data to and receiving data from online service 58; permission control 232 may be configured to block device 50e from transmitting data but to permit receiving data from online service 58.

In some embodiments, at least one permission control may be configured to control the exchange of data between the sample collection device and one or more data acquisition and transmission devices.

Figure 12:
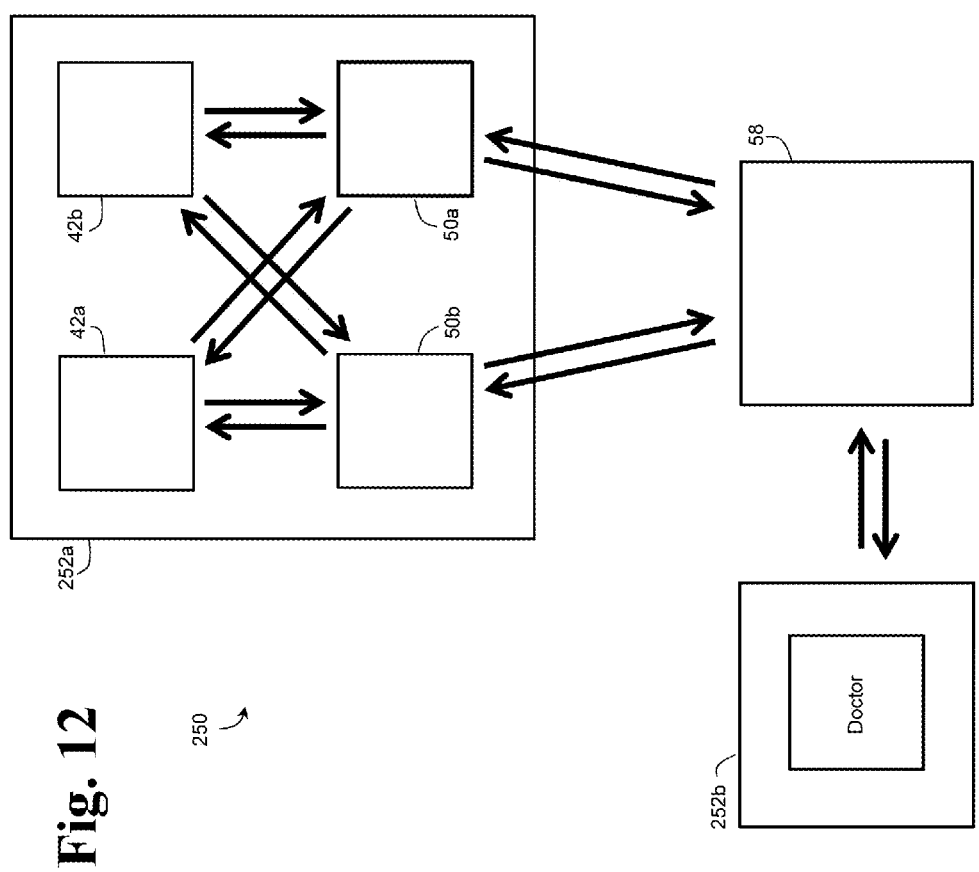
FIG. 12 depicts another illustrative embodiment of the diagnostic system of FIG. 1.

FIG. 12 depicts an embodiment of a diagnostic system, generally indicated at 250, according to aspects of the present disclosure. Diagnostic system 250 may include a local system 252a, such as a household, and may also include an additional local system 252b, such as a medical office. Local system 252a may include one or more patients, one or more sample collection devices, such as sample collection devices 42a and 42b, and one or more data acquisition and transmission devices, such as devices 50a and 50b. As shown, devices 50a and 50b may both manage data within local system 252a. However, at least one device, such as device 50b, may be blocked from transmitting and/or receiving data related to one or both patients. The configuration of local system 252a may include any suitable and/or desirable combination of one or more patients, one or more sample collection devices, one or more data acquisition and transmission devices, one or more permission controls, and/or one or more links to online service 58. As shown, both devices 50b and 50a link to online service 58, but data acquisition and transmission devices in local system 252a may additionally or alternatively link to an intermediary device or a data processing location other than online service 58. As shown, local system 252b may be in communication with local system 252a regarding data from diagnostic system 250 via online service 58 and may further include permission controls (not shown).

Figure 13:
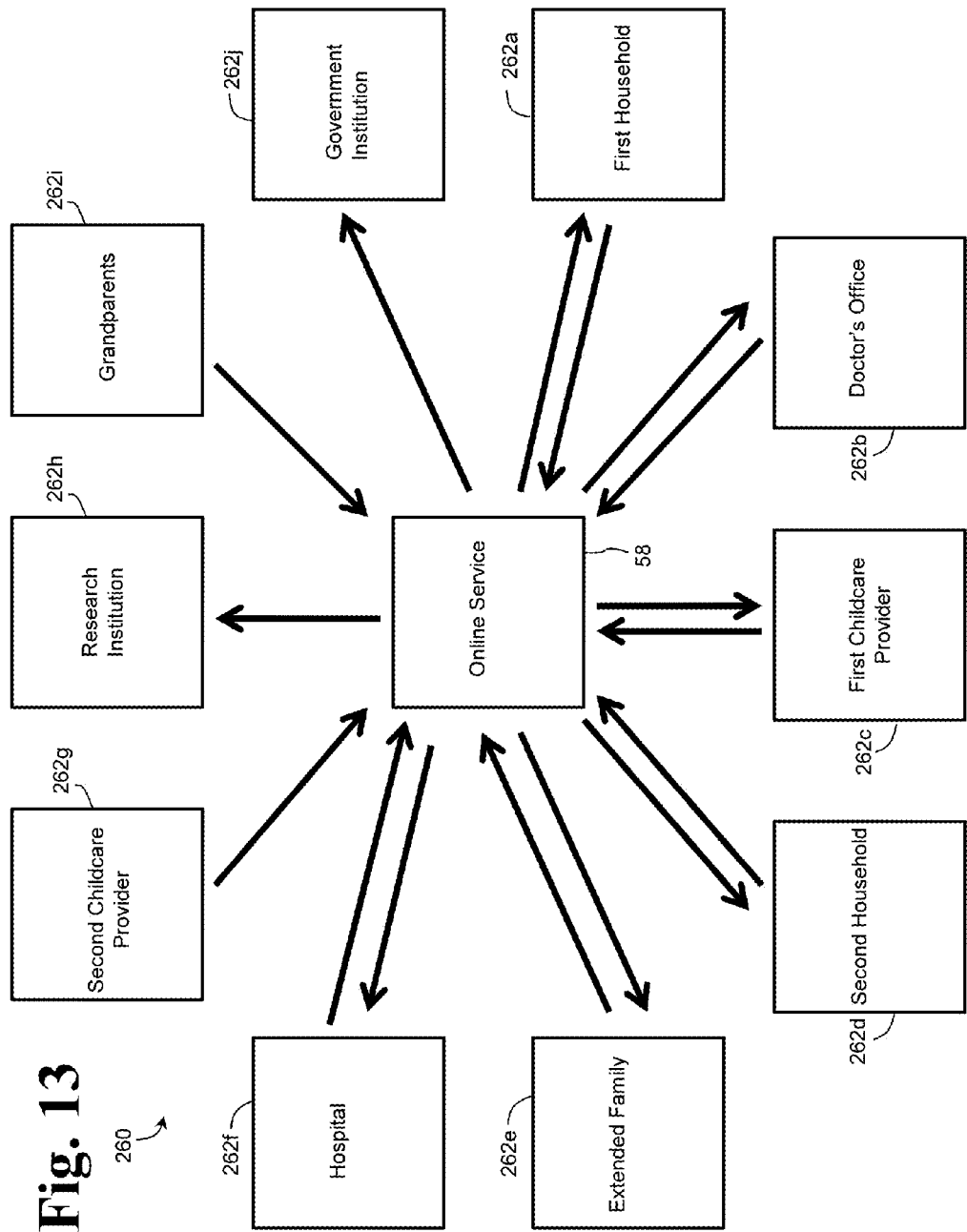
FIG. 13 depicts another illustrative embodiment of the diagnostic system of FIG. 1.

FIG. 13 depicts an embodiment of a diagnostic system, generally indicated at 260, according to aspects of the present disclosure. As shown, diagnostic system 260 may include multiple local systems. For example, diagnostic system 260 may include local systems of varying configurations and/or purposes, such as a first household 262a, a doctor's office 262b, a first childcare provider 262c, a second household 262d, an extended family 262e, a hospital 262f, a second childcare provider 262g, a research institution 262h, grandparents 262i, and a government institution 262j. As shown, local systems 262a, 262b, 262c, 262d, 262e, and 262f may receive data from and send data to online service 58, and may further include read and/or write capabilities. Also as shown, local systems 262g and 262i may only send data to online service 58, and the local systems 262h and 262j may only receive data from online service 58, all of which may or may not individually include read and/or write capabilities. It should be appreciated that diagnostic system 260 is not limited to these exemplary local systems and/or these types of local systems. Rather, diagnostic system 260 may include any suitable number and/or types of local systems for acquiring, transmitting, analyzing, processing, and/or storing diagnostic data.

Each local system may include at least one sample collection device, at least one data acquisition and transmission device, a patient, and/or at least one interested party.

By including multiple local systems in the diagnostic system it may be possible to track diagnostic trends, such as urine content, over time, geographic areas, and/or populations. Furthermore, the inclusion of multiple local systems may make it so a patient and/or his or her caregiver may share information related to patient sample content, such as patient urine content. It should also be appreciated that diagnostic system 260 may aid in conducting epidemiological analysis.

Figure 14:
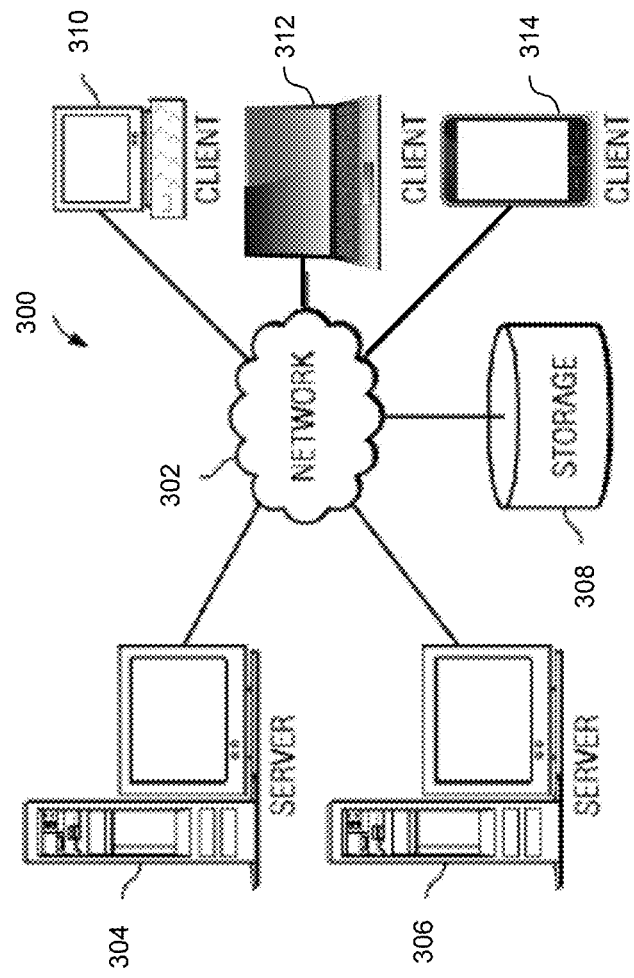
FIG. 14 is a pictorial representation of a distributed data processing system in which illustrative embodiments may be implemented.
Figure 15:
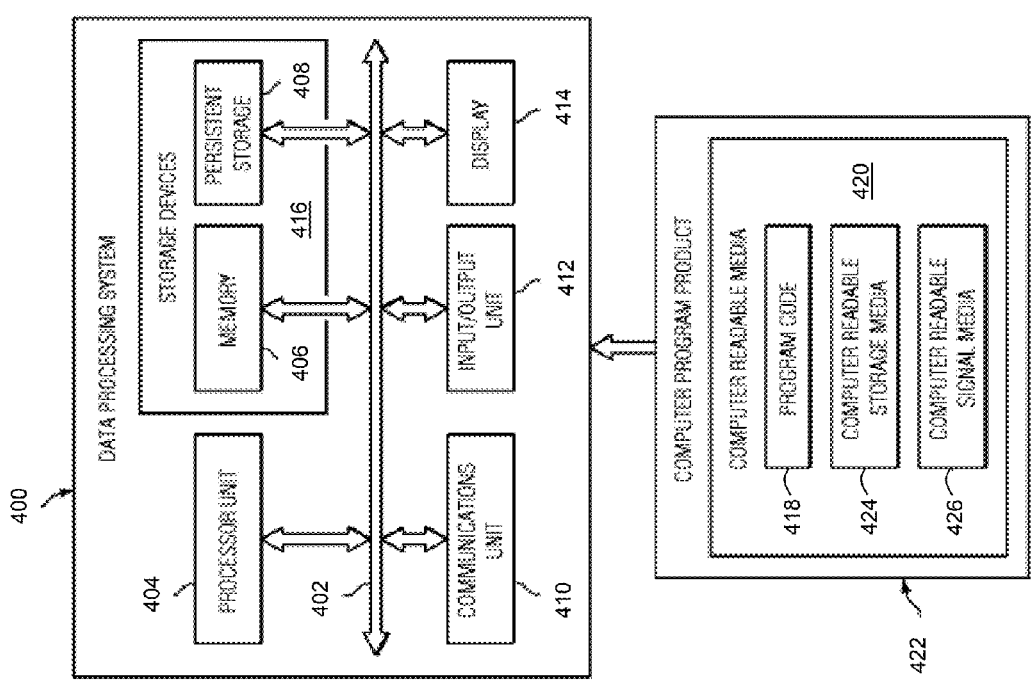
FIG. 15 is a block diagram of a data processing system in which illustrative embodiments may be implemented.

In general reference to FIGS. 14-15, as will be appreciated by one skilled in the art, the present disclosure may be embodied as a system, method, or computer program product. Accordingly, the disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the disclosure may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples of a computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device.

Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of the present disclosure, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, or RF.

Computer program code for carrying out operations of the embodiments of the disclosure may be written in any combination of one or more programming languages, including an object oriented programming language such as Java, Smalltalk, C++ or the like and conventional procedural programming languages, such as the C programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The aspects of the disclosure are described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create ways of implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instructions which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

With reference now to the figures and in particular with reference to FIG. 14, an illustrative diagram of a data processing environment is provided in which illustrative embodiments may be implemented. It should be appreciated that FIG. 15 is only provided as an illustration of one implementation and is not intended to imply any limitation with regard to the environments in which different embodiments may be implemented. Many modifications to the depicted environments may be made.

FIG. 14 depicts a pictorial representation of a distributed data processing systems in which illustrative embodiments may be implemented. Network data processing system 300 is a network of computers in which the illustrative embodiments may be implemented. Network data processing system 300 contains network 302, which is the medium used to provide communications links between various devices and computers connected together within network data processing system 300. Network 302 may include connections, such as wire, wireless communication links, or fiber optic cables.

In the depicted example, server computer 304 and server computer 306 connect to network 302 along with storage unit 308. In addition, client computers 310, 312, and 314 connect to network 302. Client computers 310, 312, and 314 may be, for example, personal computers, network computers, or mobile computing devices such as personal digital assistants (PDAs), cell phones, smartphones, handheld gaming devices, or tablet computers and the like. In the depicted example, server computer 304 provides information, such as boot files, operating system images, and applications to client computers 310, 312, and 314. Client computers 310, 312, and 314 are clients to server computer 304 in this example. Network data processing system 300 may include additional server computers, client computers, and other devices not shown.

Program code located in network data processing system 300 may be stored on a computer recordable storage medium and downloaded to a data processing system or other device for use. For example, program code may be stored on a computer recordable storage medium on server computer 304 and downloaded to client computer 310 over network 302 for use on client computer 310.

In the depicted example, network data processing system 300 is the Internet with network 302 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, that includes thousands of commercial, governmental, educational and other computer systems that route data and messages. Network data processing system 300 also may be implemented as a number of different types of networks, such as for example, an intranet, a local area network (LAN), or a wide area network (WAN). FIG. 14 is intended as an example, and not as an architectural limitation for the different illustrative embodiments.

Turning now to FIG. 15, a block diagram of a data processing system is depicted in accordance with the present disclosure. In this illustrative example, data processing system 400 includes communications fabric 402, which provides communications between processor unit 404, memory 406, persistent storage 408, communications unit 410, input/output (I/O) unit 412, and display 414.

Processor unit 404 serves to execute instructions for software that may be loaded into memory 406. Processor unit 404 may be a number of processors, a multi-processor core, or some other type of processor, depending on the particular implementation. A number, as used herein with reference to an item, may refer to one or more items. Further, processor unit 404 may be implemented using a number of heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device is any piece of hardware that is capable of storing information, such as, for example, without limitation, data, program code in functional form, and/or other suitable information on either a temporary basis and/or a permanent basis. Memory 406, in these examples, may be, for example, a random access memory or any other suitable volatile or non-volatile storage device. Persistent storage 408 may take various forms, depending on the particular implementation.

For example, persistent storage 408 may contain one or more components or devices such as a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 may be a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard, a mouse, and/or some other suitable input device. Further, input/output unit 412 may send output to a printer. Display 414 provides a mechanism to display information to a user.

Instructions for the operating system, applications, and/or programs may be located in storage devices 416, which are in communication with processor unit 404 through communications fabric 402. In these illustrative examples, the instructions are in a functional form on persistent storage 408. These instructions may be loaded into memory 406 for execution by processor unit 404. The processes of the different embodiments may be performed by processor unit 404 using computer implemented instructions, which may be located in a memory, such as memory 406.

These instructions are referred to as program code, computer usable program code, or computer readable program code that may be read and executed by a processor in processor unit 404. The program code in the different embodiments may be embodied on different physical or computer readable storage media, such as memory 406 or persistent storage 408.

Program code 418 is located in a functional form on computer readable media 420 that is selectively removable and may be loaded onto or transferred to data processing system 400 for execution by processor unit 404. Program code 418 and computer readable media 420 form computer program product 422 in these examples. In one example, computer readable media 420 may be computer readable storage media 424 or computer readable signal media 426. Computer readable storage media 424 may include, for example, an optical or magnetic disk that is inserted or placed into a drive or other device that is part of persistent storage 408 for transfer onto a storage device, such as a hard drive, that is part of persistent storage 408. Computer readable storage media 424 also may take the form of a persistent storage, such as a hard drive, a thumb drive, or a flash memory, that is connected to data processing system 400. In some instances, computer readable storage media 424 may not be removable from data processing system 400. In these illustrative examples, computer readable storage media 424 is a non-transitory computer readable storage medium.

Alternatively, program code 418 may be transferred to data processing system 400 using computer readable signal media 426. Computer readable signal media 426 may be, for example, a propagated data signal containing program code 418. For example, computer readable signal media 426 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical and/or wireless in the illustrative examples.

In some embodiments, program code 418 may be downloaded over a network to persistent storage 408 from another device or data processing system through computer readable signal media 426 for use within data processing system 400. For instance, program code stored in a computer readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different advantageous embodiments may be implemented in a data processing system including components in addition to or in place of those illustrated for data processing system 400. Other components shown in FIG. 15 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

As another example, a storage device in data processing system 400 may be any hardware apparatus that may store data. Memory 406, persistent storage 408, and computer readable media 420 are examples of storage devices in a tangible form.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 406, or a cache such as found in an interface and memory controller hub that may be present in communications fabric 402.

It is understood that all or part of the system(s) and/or method(s) of the present disclosure may be implemented and/or utilized in a cloud computing environment.

Embodiments of Diagnostic Methods

Figure 16:
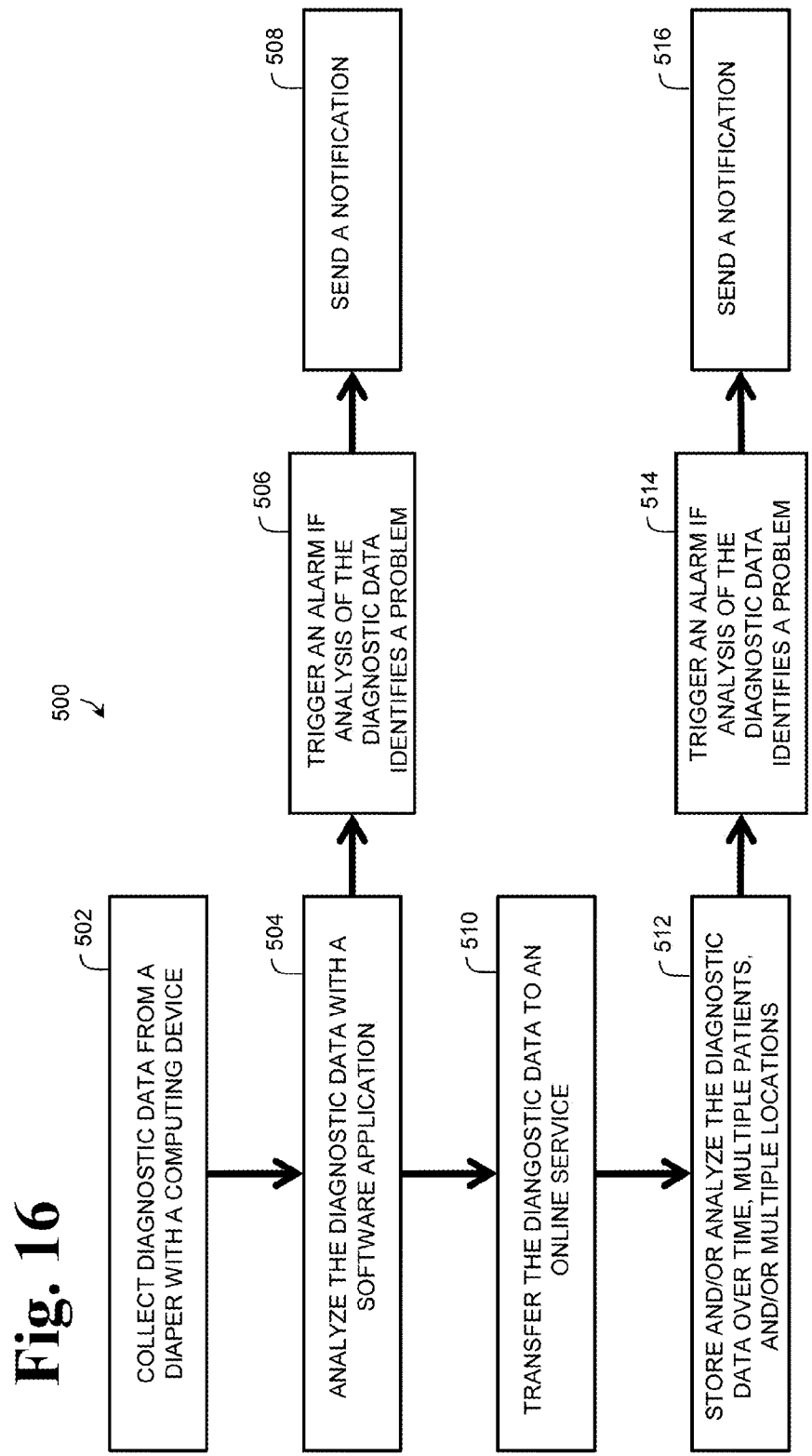
FIG. 16 is a flow-chart depicting a method of use of the diagnostic system of FIG. 1.

FIG. 16 depicts a method, generally indicated at 500, of using a diagnostic system, according to aspects of the present disclosure. Method 500 may include a step 502 of collecting diagnostic data (e.g., urine content data) from a diaper with a smartphone or any other suitable imaging device. Method 500 may include a step 504 of analyzing the diagnostic data with a software application, which may be running on the smartphone and/or a network (e.g., online service), which may include one or more computers. Method 500 may include a step 506 of triggering an alarm (e.g., initiating a notification) if analysis of the diagnostic data in step 504 identifies a problem (e.g., an abnormal health condition). In step 506, an application running on the smartphone may trigger the alarm and/or an application running on the network may trigger the alarm. Method 500 may include a step 508 of sending an appropriate notification to the user. For example, the notification may indicate to the user that a subject who produces a sample collected by the diaper may have the abnormal health condition and that attention from a health care professional should be sought.

Method 500 may include a step 510 of transferring the diagnostic data to the online service, and a step 512 of storing and/or analyzing the diagnositc data over time, multiple patients, and/or multiple locations.

Method 500 may include a step 514 of triggering an alarm if analysis of the diagnostic data in step 512 identifies a problem (e.g., an abnormal health condition of a specific subject, or a specific population), and a step 516 of sending an appropriate notification (e.g., to the specific subject, or the specific population). In step 516, the appropriate notification may be associated with the identified problem (e.g., may describe the abnormal health condition, and/or instruct the specific subject, or specific population to seek medical attention). In some embodiments of method 500, sending the appropriate notification may involve sending the appropriate notification to another local system, such as a governmental institution or a local hospital.

It should be appreciated that anything that happens on the smartphone, or any other suitable device, may additionally or alternatively happen in the online service and anything that happens in the online service may additionally or alternatively happen on the smartphone, or any other suitable device.

In some embodiments a method of use may include putting a diaper, which may be coupled to a diagnostic test in such a way as to collect an appropriate sample, such as urine, on a baby and waiting for the baby to produce the appropriate sample, such as urine. The method may also include accessing the diagnostic test after it has been exposed to the appropriate sample(s), such as removing the diagnostic test from the diaper if it is inserted therein or appropriately turning the baby if the diagnostic test is coupled to the diaper in such a way as to allow visual access without removing the diaper from the baby, such as if the diagnostic test is coupled to an absorbent core and positioned on the front of the diaper with a transparent film providing visual access.

The method may also include indicating an error in the diagnostic testing with a control in a way similar to that of a pregnancy test.

The method may further include taking a photo of the diagnostic test with a smartphone. The method may also include opening a software application on the smartphone, in which a user can manage patients, manage one or more diagnostic(s) to be performed, and/or collect and/or manage data from one or more diagnostic test(s) such as taking one or more photo(s) of the diagnostic test(s), adding a timestamp, datestamp, patient identifier, and/or caregiver identifier.

The method may further include the software application analyzing one or more photos to extract data related to the diagnostic test(s), notifying a user regarding the analysis of the data, such as with notification of a potential problem, method of care, and/or other advice, storing the data locally and/or in an online service or network, and displaying the data in any suitable format, such as with a chart, graph, percentiles, and/or in comparison to a standard.

Moreover, the method may include uploading data related to the diagnostic test to the online service or network, which may include one or more computer(s), one or more database(s), one or more server(s), one or more software application(s), and/or one or more connection(s). The method may include the online service or network analyzing diagnostic data from one or more diagnostic test(s) from one or more patient(s), storing the diagnostic data and related data, allowing the user and/or a healthcare provider to share and communicate about the data, and/or notifying the user regarding analysis of the data, such as with notification of a potential problem, method of care, and/or other advice. The method may further include analyzing data over time to determine a trend and/or conduct an epidemiological study. It should be appreciated that the method may include automatic retrieval of data, in which the user does not have to manually enter sample content data.

In some embodiments, a caregiver may put a diaper on a baby. The diaper may have a diagnostic test removably coupled to the diaper or inserted into and/or onto the diaper in such a way as to be exposed to an appropriate sample, such as urine. The caregiver may then wait for the diagnostic test to be exposed to the sample. For example, a diagnostic urine test may be coupled to an absorbent core of the diaper on a front of the diaper through a cut-out with a transparent seal covering the diagnostic test. The caregiver may wait for the baby to produce urine and for the urine to permeate a polypropylene sheet which may be coupled to the diagnostic test and for the diagnostic test to produce content data from the sample (e.g., based on one or more analytes contained in the sample).

The caregiver may then access a software application on a smartphone, which may guide the caregiver in managing patients, patient information, diagnostic information, and/or how to take a photo of the diagnostic test. The caregiver may take a photo of the diagnostic test and the software application may indicate to the caregiver whether or not the photo is sufficient for collecting appropriate data from the diagnostic test. The caregiver may then upload the photo to an online service through the software application. The software application may indicate to the caregiver that the caregiver or other interested party may be notified of a problem recognized by the diagnostic test.

In some embodiments, the software application may be configured to automatically acquire a photo of the diagnostic test (e.g., in an embodiment of a diagnostic test including a machine-readable code). The software application may be configured to automatically analyze the photo and upload the photo to the online service according to instructions included in the machine-readable code.

The software application may indicate to the caregiver whether or not the photo was uploaded successfully. The online service may then analyze the photo to extract sample content data from the diagnostic test and thus monitor the health of the baby.

The online service may then keep track of and analyze the data received by the online service over time to identify trends or issues related to the diagnostic testing being performed. The trends or issues may be specific to the subject being tested, and/or related to all subjects in the same household, geographic location, age, gender, etc.

The online service may notify the caregiver or other interested party, such as the baby's doctor, concerning the baby's health, and may allow the caregiver and the interested party to share information. The online service may store the data in a database and analyze the data over multiple timeframes to identify trends. The online service may be similarly connected to multiple patients from multiple geographical locations, which may aid in conducting epidemiological studies.

A method of health screening/monitoring, according to aspects of the present disclosure, may include a step of providing a computing system having a memory, and a step of disposing a first diaper on a subject at a first point in time, the first diaper including a first set of one or more sensors configured to detect contents of bodily waste produced by the subject.

The method of health screening/monitoring may include a step of waiting for the subject to produce a first portion of bodily waste, a step of acquiring a first image of the first set of one or more sensors at a second point in time, a step of analyzing the first image with the computing system to produce a first health screening data point based on contents (e.g., one or more analytes) of the first portion of bodily waste produced by the subject between the first and second points in time, and a step of storing the first health screening data point in the memory.

The method of health screening/monitoring may include a step of disposing a second diaper on the subject at a third point in time, the second diaper including a second set of one or more sensors configured to detect contents of bodily waste produced by the subject, a step of waiting for the subject to produce a second portion of bodily waste, a step of acquiring a second image of the second set of one or more sensors at a fourth point in time, and a step of analyzing the second image with the computing system to produce a second health screening data point based on contents of the second portion of bodily waste produced by the subject between the third and fourth points in time.

The method of health screening/monitoring may include a step of storing the second health screening data point in the memory, and a step of determining whether the first and second health screening data points indicate an abnormal health condition of the subject.

The method of health screening/monitoring may include a step of the computing system sending a notification to a user if the first and second health screening data points indicate the abnormal health condition.

In the method of health screening/monitoring, the bodily waste may be urine and the abnormal health condition may be dehydration, in which case the first data point may include a first specific gravity of urine produced by the subject between the first and second points in time, the second data point may include a second specific gravity of urine produced by the subject between the third and fourth points in time, and the determining step may involve determining whether the first and second specific gravities each exceed a predetermined threshold level (e.g., a specific gravity of approximately 1.2).

In the method of health screening/monitoring, the bodily waste may be urine and the abnormal health condition may be diabetic ketoacidosis, in which case the computing system may be configured to send the notification to the user if both the first and second health screening data points indicate that the urine of the subject contains at least one component selected from a group of components comprising ketones and glucose.

Embodiments of Methods of Manufacture

Figure 17:
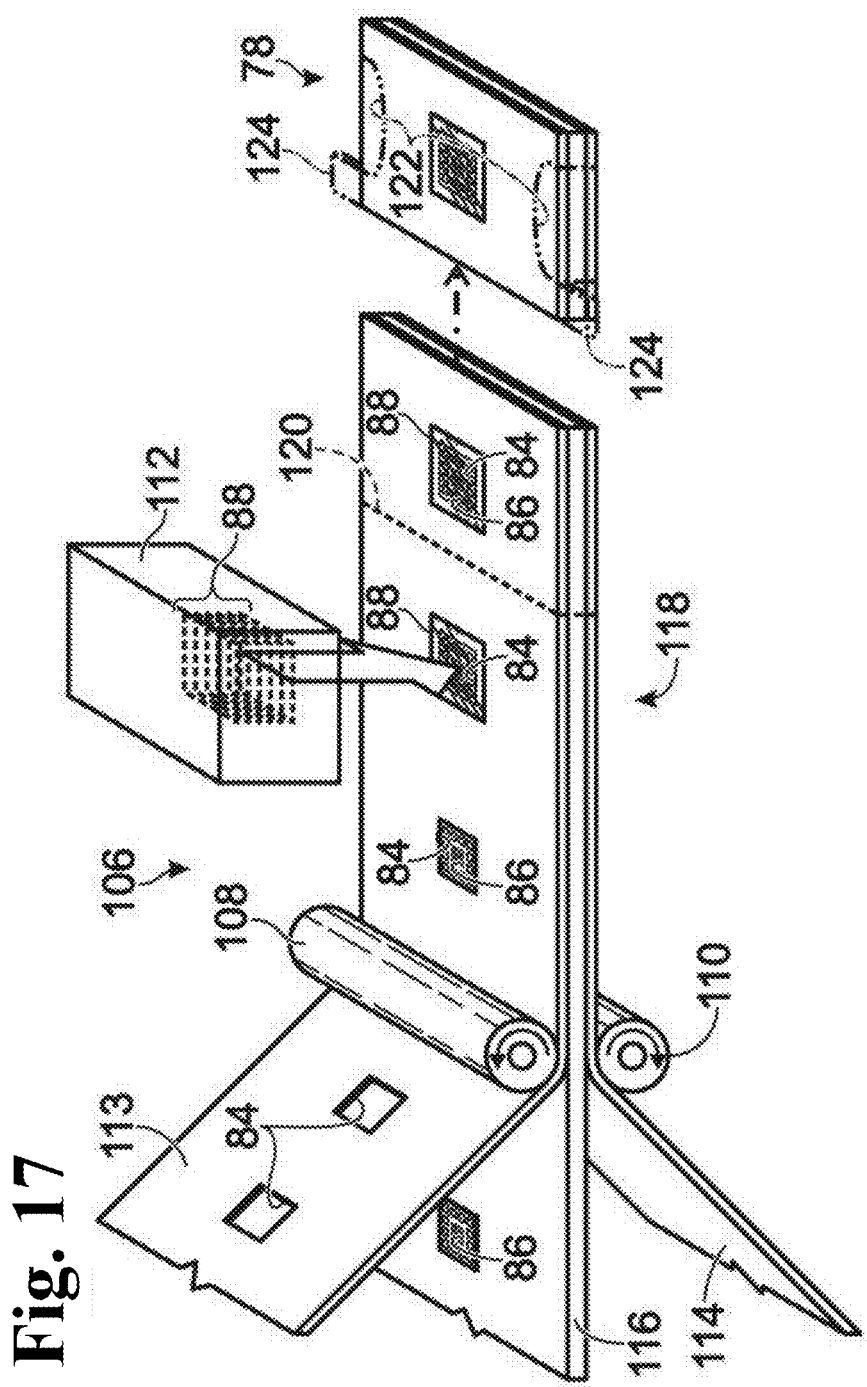
FIG. 17 depicts an embodiment of an apparatus for manufacturing a sample collection device.

FIG. 17 depicts an apparatus, generally indicated at 106, for manufacturing diaper 78. Apparatus 106 may include a first roller 108, a second roller 110, and an applicator machine 112.

As shown in FIG. 17, apparatus 106 may provide an outer layer web 113, an inner layer web 114, and a sheet 116 upon which a plurality of diagnostic tests 86 are disposed. Outer layer web 113 may include a waterproof layer, such as waterproof layer 80 (see FIG. 3) and/or any other suitable layers of diaper 78. Inner layer web 114 may include a permeable layer, such as permeable layer 89 (see FIG. 3) and/or any other suitable layers of diaper 78. Sheet 116 may be a polypropylene sheet treated to acquire a hydrophilic property, or may be another nonwoven material with a hydrophilic property. In some embodiments, sheet 116 may include an absorbent layer, such as absorbent core 82 (see FIG. 3).

A first portion of apparatus 106, such as a first die cutter (not shown) or other suitable mechanism or device, may form a plurality of cut-outs 84 in outer layer web 113 at regular intervals.

First and second rollers 108 and 110 (and/or any other suitable mechanism) may continuously roll sheet 116 between outer layer web 113 and inner layer web 114. First and second rollers 108 and 110 (and/or any other suitable mechanism) may join together outer layer and inner layer webs 113 and 114 to form a package, generally indicated at 118. In some embodiments, joining together outer layer and inner layer webs 113 and 114 may involve sandwiching sheet 116 between outer layer and inner layer webs 113 and 114 to position the plurality of diagnostic tests 86 in the plurality of cut-outs 84.

Applicator machine 112 may be configured to apply transparent tape 88 onto package 118. For example, applicator machine 112 may be configured to dispose transparent tape 88 over each of diagnostic tests 86 and out layer web 113 to seal respective cut-outs 84 (e.g., to seal diagnostic tests 86 in respective cut-outs 84).

Typically outer layer web 113 is dyed or bleached during normal production. However in some embodiments, outer layer web 113 may be transparent (e.g., substantially or completely clear, and may not be dyed or bleached), in which case outer layer web 113 may not include cut-outs 84 and diagnostic tests 86 may be sandwiched between sheet 116 and outer layer web 113.

A second portion of apparatus 106, such as a second die cutter (not shown) or any other suitable mechanism or device, may separate and/or shape the package into a plurality of diapers 78. For example, after applicator machine 112 has applied transparent tape 88 to the portion of package 118 the second portion of apparatus 106 may make a plurality of cuts 120 in a portion of package 118. In some embodiments, the second portion of apparatus 106 may be configured to couple elastic and/or other components to package 118, so as to form leg recesses 122 and/or attachment tabs 124 in each of diapers 78.

Figure 18:
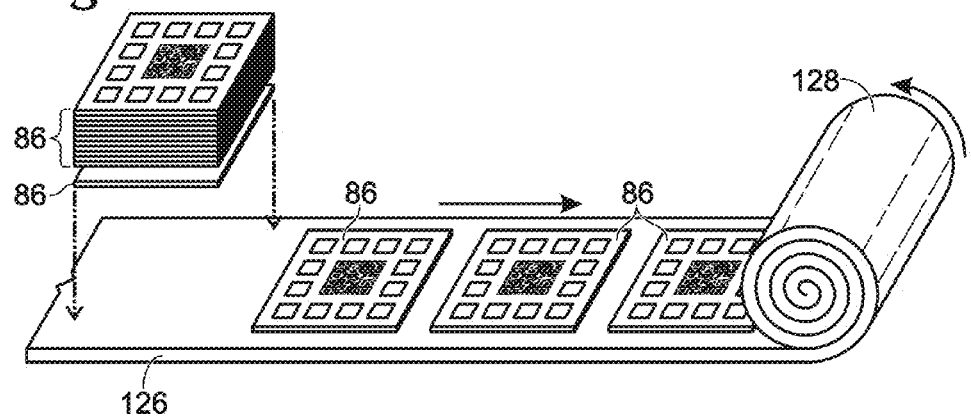
FIG. 18 depicts diagnostic tests being disposed on a sheet and the sheet being wound into a roll, according to aspects of the present disclosure.

FIG. 18 shows a plurality of diagnostic tests 86 being disposed on a sheet 126, and sheet 126 being wound into a roll 128. Sheet 126 may be made of a similar material as sheet 116 (see FIG. 17).

Figure 19:
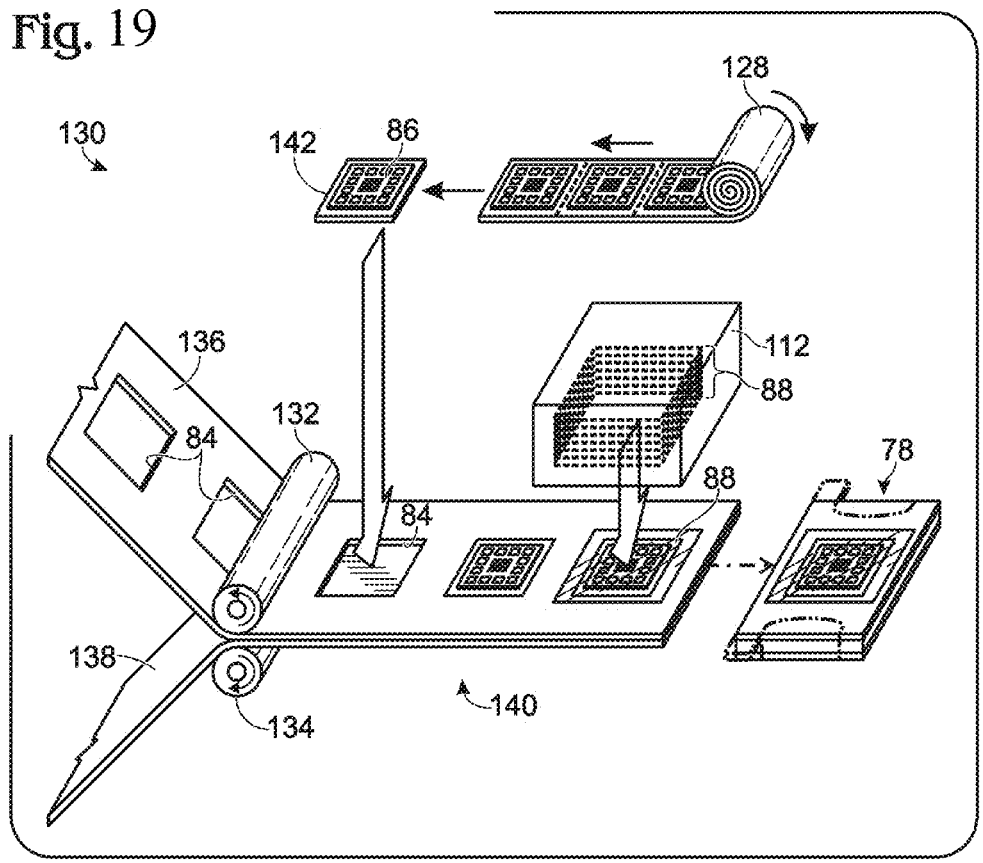
FIG. 19 depicts another embodiment of an apparatus for manufacturing a sample collection device.

FIG. 19 depicts another apparatus, generally indicated at 130, for manufacturing diaper 78. As shown, apparatus 130 may include a first roller 132, a second roller 134, applicator machine 112, and may provide an outer layer web 136, and an inner layer web 138.

A first portion of apparatus 130 may form a plurality of cut-outs 84 at regular intervals in outer layer web 136. Outer layer web 136 may include a waterproof layer, and inner layer web 138 may include an absorbent layer and a permeable layer. Outer layer and inner layer webs may be described as regular diaper layers.

Rollers 132 and 134 may join together outer and inner layer webs 136 and 138 to form a package, generally indicated at 140.

A second portion of apparatus 130 may unwind and cut roll 128 into a plurality of patches 142, with each patch including at least one diagnostic test or panel 86. The second portion of apparatus 130 may position each patch into one of the respective cut-outs 84. Applicator machine 112 may dispose transparent tape 88 over each patch and outer layer web 136 to seal cut-outs 84.

A third portion of apparatus 130 may separate and/or form package 140 into a plurality of diapers 78.

Figure 20:
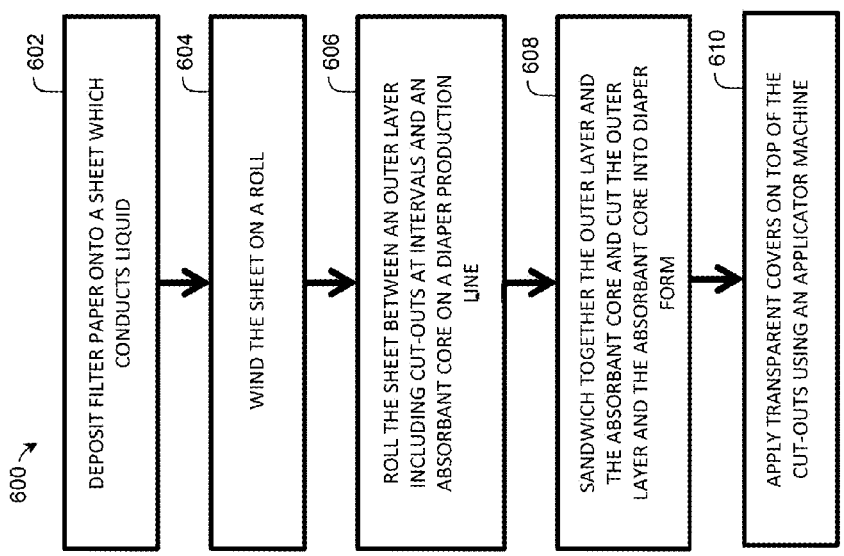
FIG. 20 is a flow-chart depicting an illustrative embodiment of a method of manufacturing a diaper, according to aspects of the present disclosure.

FIG. 20 depicts an illustrative method, generally indicated at 600, of manufacturing a diagnostic diaper, according to aspects of the present disclosure. Method 600 may include a step 602 of depositing filter paper (e.g., diagnostic filter paper impregnated with one or more reagents configured to detect one or more analytes in a sample) onto a polypropylene (or other suitable material) sheet, such as Hanes Industries Elite 075 White #49616, which conducts liquid. Suitable filter paper may be obtained from Marcherey-Nagel GmbH & Co. KG. The filter paper may be diced into squares (or other suitable shapes), such as those on urine analysis strips available from 11 PARAMETERS ULTRA® Test Strips from BTNX, Inc. or Siemens MULTISTIX® or other urine analysis strips. In some embodiments, the diagnostic diaper may include another suitable sensing material configured as desired.

Method 600 may include a step 604 of winding the polypropylene sheet on a roll, and a step 606 of rolling the polypropylene sheet (in some embodiments continuously or substantially continuously) between an outer layer including cut-outs at (in some embodiment regular or substantially regular) intervals and an absorbent core on a diaper production line.

Method 600 may include a step 608 of sandwiching together the outer layer and the absorbent core, which may form a package. Step 608 may involve cutting the outer layer and the absorbent core into diaper form.

Method 600 may include a step 610 of applying a transparent cover (e.g. tape, such as OPSITE® FLEXIFIX®) or other suitable substantially transparent material, on top of the cut-outs using an applicator machine. In some embodiments of method 600, step 610 may be carried out after the sandwiching of step 608 but prior to the cutting of step 608.

Figure 21:
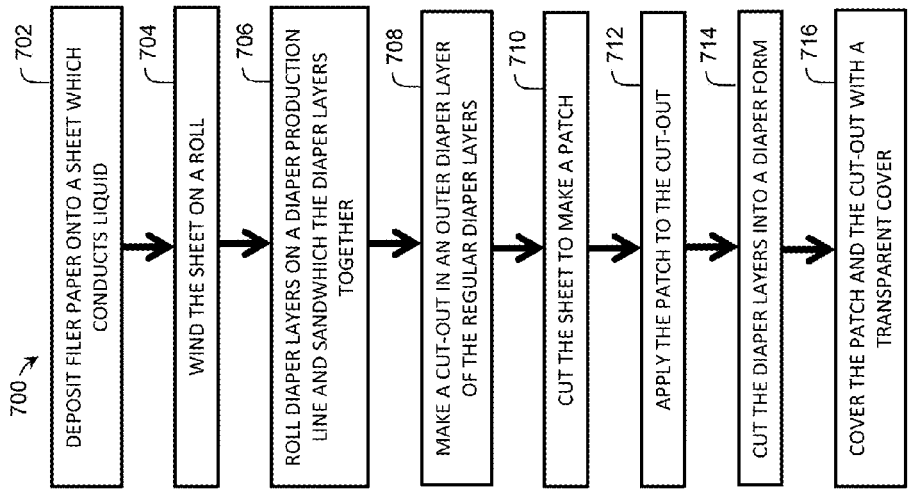
FIG. 21 is a flow-chart depicting another illustrative embodiment of a method of manufacturing a diaper, according to aspects of the present disclosure.

FIG. 21 depicts another illustrative method, generally indicated at 700, of manufacturing a diagnostic diaper, according to aspects of the present disclosure. Method 700 may include a step 702 of depositing diagnostic filter paper onto a polypropylene (or other suitable material) sheet, which conducts liquid.

Method 700 may include a step 704 of winding the polypropylene sheet on a roll, and a step 706 of rolling regular diaper layers on a diaper production line and sandwiching the regular diaper layers together to form a package.

Method 700 may include a step 708 of making (or forming) a cut-out in an outer diaper layer of the regular diaper layers, a step 710 of cutting the polypropylene sheet to make a patch, and a step 712 of applying the patch to the cut-out.

Method 700 may include a step 714 of cutting the regular diaper layers (e.g., the package) into a diaper form, and a step 716 of covering the patch and the cut-out with a transparent cover (e.g. tape or any other suitable substantially transparent film). In some embodiments of method 700, the covering of step 716 may be carried out prior to the cutting of step 714.

Figure 22:
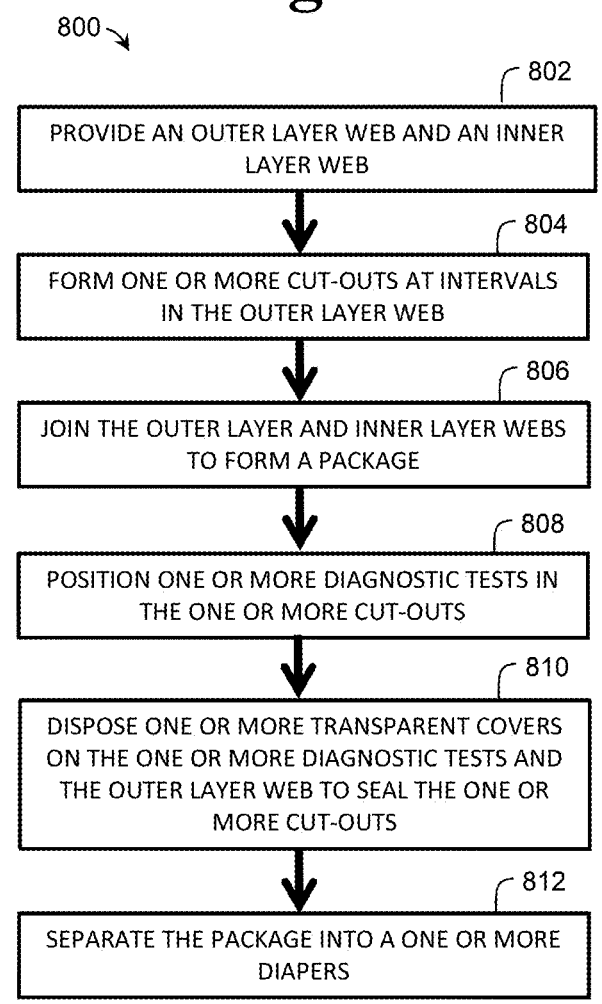
FIG. 22 is a flow-chart depicting another illustrative embodiment of a method of manufacturing diapers, according to aspects of the present disclosure.

FIG. 22 depicts another illustrative method, generally indicated at 800, of manufacturing diapers, according to aspects of the present disclosure. Method 800 may include a step 802 of providing an outer layer web and an inner layer web, a step 804 of forming one or more cut-outs at (in some embodiments regular or substantially regular) intervals in the outer layer web, and a step 806 of joining the outer layer and inner layer webs to form a package.

Method 800 may include a step 808 of positioning one or more diagnostic tests in the one or more cut-outs, a step 810 of disposing a transparent cover (e.g. tape) on the diagnostic tests and the outer layer web to cover and/or seal the cut-outs, and a step 812 of separating the package into one or more diapers.

In some embodiments of method 800, the positioning of step 808 may be carried out prior to the joining of step 806. For example, step 808 may involve disposing the plurality of diagnostic tests on a sheet, and (in some embodiments continuously or substantially continuously) rolling the sheet between the outer layer and inner layer webs prior to the joining step.

In other embodiments of method 800, the positioning step may involve providing a sheet on which the one or more diagnostic tests are disposed, cutting the sheet into one or more patches, wherein each patch includes at least one of the diagnostic tests, and placing the one or more patches into the one or more cut-outs.

Possible Advantages of Embodiments of the Invention

The present disclosure may provide one or more advantages, such as the ones described herein and below.

By creating diapers with embedded diagnostic sensors, such as filter paper, to detect levels of glucose, bilirubin, ketone, specific gravity, blood, pH, protein, urobilinogen, nitrite, leukocytes, creatinine, and other factors in urine, and by automatically uploading this information to an online service, online software may infer possible disease states by analyzing changes in urine content over short (several days) and long (months or years) periods of time. The online software may then recommend further monitoring, additional testing, or seeking of medical care. In addition to analyzing data from the same patient over time, the online software may also compare data between patients of similar ages and in close locations, pointing out if multiple people within the same geographical area and in a similar age group are exhibiting similar deviations from normal physiology. The online software may also utilize a patient's medical history, such as number of fevers or other condition exhibited by the patient in a predefined prior period (e.g., six months), patient family's medical history, such as prevalence of type 1 diabetes, and current variables, such as presence of fever in the patient.

Previously, patients and physicians typically relied on dipping urine analysis strips into a cup with urine when other symptoms of disease were already prominent. The present teaching discloses a sample collection device (e.g., a diaper or incontinence pad) with embedded diagnostic sensors that may utilize a re-usable wireless transmitter or a camera-phone application to transmit sensor information to an online service that may analyze diagnostic data and may perform trend and statistical analysis on multiple data points across time and/or from different patients.

Receiving systems that work with existing sensor-enabled diapers are capable of raising an alarm, but not of long-term monitoring and analysis of diagnostic data collected from many patients over time. Urine analysis strips often read out five to ten variables and physicians often don't have access to an online database or even a standardized form to record the data. Moreover, generally healthy patients rarely present themselves to physicians more than once per year, making monitoring difficult.

The present teaching enables monitoring of urine content, as well as trend and statistical analysis that may identify slow changes in hydration and kidney function, impending infections, and other potential metabolic and endocrine disease states. By tracking other data such as age and geographic location, it may also enable identification of potential disease epidemics.

By using one diaper, disclosed in the present teaching, per day, a caregiver may understand over a period of time whether the child may be becoming dehydrated, developing an infection, and/or developing endocrine and/or metabolic problems. The caregiver may be advised whether the child may need simple attention, which may be given by the caregiver (e.g., more fluids), may need further monitoring (with or without use of the diapers—such as looking for a rash or measuring temperature, or additional monitoring using diapers), and/or may need to seek immediate physician attention for diagnosis and/or help.

Frequently, patients in long-term care facilities or under nursing care at home may be diagnosed with co-morbidities late because they are not often given the care and attention that they may require. Automating urine analysis to detect new co-morbidities or progress of existing conditions may improve their quality of life and may reduce the total cost of their care. Patients in long-term care facilities or under nursing care at home have a high incidence of urinary tract infections. Many such infections are difficult to diagnose because the patients may be developing memory loss and/or dementia and may be difficult to communicate with, and because their immune systems may be too weak to exhibit a response that can be observed as a fever. Such patients may be either under-diagnosed or are perpetually prescribed a low dose of antibiotic medicine. Automating urine analysis to detect urinary tract infections may improve the quality of life and may reduce the total cost of care of these patients.

Although described embodiments have been shown and described with reference to the foregoing operational principles and embodiments, it will be apparent to those skilled in the art that various changes in form and detail may be made without departing from the spirit and scope of the invention. The present invention is intended to embrace all such alternatives, modifications and variances that fall within the scope of the appended claims.

It is believed that the disclosure set forth above encompasses multiple distinct inventions with independent utility. While each of these inventions has been disclosed in its form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

Inventions embodied in various combinations and sub-combinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

The following paragraphs may describe one or more embodiments according to the present disclosure.

A health monitoring system, comprising a computing system having a processor, a memory, and a health monitoring system program including a plurality of instructions stored in the memory that are executed by the processor to: receive and store a first digital data packet that includes a first sample reading, collected at a first time interval, of a first diagnostic test of a first diaper configured to detect an analyte in bodily waste excreted by a subject, wherein the first sample reading includes data corresponding to an amount of the analyte detected in the first diagnostic test and the first time interval at which the first sample was collected; receive and store a second digital data packet that includes a second sample reading, collected at a second time interval different from the first time interval, of a second diagnostic test of either the first diaper or a different diaper configured to detect the analyte, wherein the second sample reading includes data corresponding to an amount of the analyte detected and the second time interval at which the second sample was collected; automatically compare the first and second sample readings against a standard for the analyte that indicates normal and abnormal levels of the detected analyte over different time intervals to analyze whether the first and second data readings correspond to an abnormal health condition of the subject based on the amount of the analyte detected in the first and second sample readings collected at the first and second time intervals; and automatically transmit an indication if there is an abnormal level of detected analyte based on analyzing the first and second sample readings.

The system of the above paragraph, further comprising a digital optical system to acquire the first and second samples by taking a visual reading of the first and second diagnostic tests and transmitting the first and second samples respectively as part of first and second digital data packets to the computing system.

The system of the above paragraph, wherein the first diaper includes a sensor in contact with the bodily waste for detecting the analyte of the first diagnostic test and a machine-readable code, proximate the sensor, configured to enable automatic, automated acquisition of digital samples by the optical sensor for the first diagnostic test.

The system of the above paragraph, wherein the plurality of instructions stored in the memory are also executed by the processor to acquire automatically a sample reading from a diagnostic test by automatically selecting a focused digital image of the sensor acquired by the digital optical system.

The system of the above paragraph, wherein the plurality of instructions stored in the memory are also executed by the processor to receive an indication from the machine-readable code indicating one or more of a format of the first diagnostic test, whether the first diagnostic test has expired past a predetermined expiration date; and an authenticity of the first diagnostic test.

The system of the above paragraph, further comprising a second sensor corresponding to the same analyte as being detected by the first sensor or a different analyte than is being detected by the first sensor.

The system of the above paragraph, wherein the plurality of instructions stored in the memory are also executed by the processor to indicate which analyte each of the first and second sensors are detecting.

The system of the above paragraph, wherein the computing system includes a first processor remote from a second processor, wherein at least one of the plurality of instructions are executed by the first processor and others of the plurality of instructions are executed by the second processor.

The system of the above paragraph, wherein the bodily waste is urine and the machine-readable code is a barcode proximate the sensor.

A health monitoring system, comprising a first diaper for collecting a first portion of bodily waste produced by a subject in a first interval of time; a first diagnostic test coupled to the first diaper, the first diagnostic test having a first set of one or more sensors configured to produce a first visual indication of one or more analytes contained in the first portion of bodily waste; and a first machine-readable code indicia proximate the first set of one or more sensors that is configured to be read by an optics system of a computing system configured to visually read the first machine-readable code to allow an application running on the computing system to perform at least one task related to a production of a first health monitoring data point based on the first visual indication.

The system of the above paragraph, wherein the computing system includes a data acquisition device, and the at least one task includes selecting a focused first digital image acquired by the data acquisition device of the first visual indication, the computing system being configured to analyze the first digital image to produce the first health monitoring data point.

The system of the above paragraph, wherein the at least one task includes identifying a format of the first set of one or more sensors.

The system of the above paragraph, wherein the at least one task includes determining whether the first diagnostic test has expired past a predetermined expiration date.

The system of the above paragraph, wherein the at least one task includes determining an authenticity of the first diagnostic test.

The system of the above paragraph, further comprising a second diaper for collecting a second portion of bodily waste produced by the subject in a second interval of time different from the first interval of time; and a second diagnostic test coupled to the second diaper, the second diagnostic test having a second set of one or more sensors configured to produce a second visual indication of one or more analytes contained in the second portion of bodily waste; wherein the data acquisition device is configured to acquire a second digital image of the second visual indication, the computing system being configured to analyze the second digital image to produce a second health monitoring data point based on the second visual indication, and to send a notification to a user if the first and second health monitoring data points are outside a predefined range.

The system of the above paragraph, wherein the first and second portions of bodily waste are respective first and second portions of urine, and the machine-readable code is a barcode disposed on the first diagnostic test.

The system of the above paragraph, wherein the computing system includes an online service having a server and a database, the data acquisition device being a digital device having a processor, a memory and a camera that is configured to transmit the first and second digital images to the server, the server being configured to analyze the first and second images to produce the first and second health monitoring data points and to store the first and second health monitoring data points in the database.

A health monitoring system, comprising a first diaper including a first diagnostic test for producing a first at least quasi-quantitative indication of a first set of one or more analytes contained in a first portion of bodily waste excreted by a subject in a first interval of time; a second diaper including a second diagnostic test for producing a second at least quasi-quantitative indication of a second set of one or more analytes contained in a second portion of bodily waste excreted by the subject in a second interval of time; and a computing system configured to visually acquire the first and second at least quasi-quantitative indications, to analyze the first and second at least quasi-quantitative indications to produce respective first and second data points, and to send a notification to a user if both the first and second data points correspond to an abnormal health condition of the subject.

The system of the above paragraph, wherein the first and second portions of bodily waste are respective first and second portions of urine, the abnormal health condition being dehydration, the first data point including a first level of specific gravity of the first portion of urine produced by the subject in the first interval of time, the second data point including a second level of specific gravity of the second portion of urine produced by the subject in the second interval of time, and the computing system being configured to send the notification to the user if both the first and second levels exceed a predetermined threshold level.

The system of the above paragraph, wherein the first and second portions of bodily waste are respective first and second portions of urine, the abnormal health condition being diabetic ketoacidosis, the computing system being configured to send the notification to the user if the first and second data points indicate that both of the first and second portions of urine contain at least one analyte that comprises one or both of a ketone or/and glucose.

The system of the above paragraph, wherein the first and second portions of bodily waste are respective first and second portions of urine, the abnormal health condition being a urinary tract infection, the computing system being configured to send the notification to the user if the first and second data points indicate that both of the first and second portions of urine contain at least one analyte that comprises one or both of a nitrite or/and leukocyte esterase.

The system of the above paragraph, wherein the first diagnostic test includes a machine-readable code configured to be visually read by the computing system to direct the computing system to perform at least one task related to the production of the first data point.

The system of the above paragraph, wherein the at least one task is selected from a group of tasks comprising: (a) selecting a focused first digital image of the first at least quasi-quantitative indication acquired by a data acquisition device of the computing system, wherein the computing system analyzes the first digital image to produce the first data point; (b) identifying a format of the first diagnostic test; (c) determining whether the first diagnostic test has expired past a predetermined expiration date; and (d) determining an authenticity of the first diagnostic test.

The system of the above paragraph, wherein the machine-readable code is a barcode disposed on the first diagnostic test.

The system of the above paragraph, wherein the computing system includes a handheld computing device and an online service, the handheld computing device being configured to visually acquire and transmit the first and second at least quasi-quantitative indications to the online service, the online service being configured to send the notification to the user via the handheld device.

A method of manufacturing diapers, comprising providing an outer layer web and an inner layer web; forming a plurality of cut-outs at regular intervals in the outer layer web; joining the outer layer and inner layer webs to form a package; positioning a plurality of diagnostic tests in the plurality of cut-outs; and separating the package into a plurality of diapers.

The method of the above paragraph, further comprising sealing transparent tape on the diagnostic tests and the outer layer web to seal the cut-outs.

The method of the above paragraph, wherein the positioning step is carried out prior to the joining step.

The method of the above paragraph, wherein the positioning step involves disposing the plurality of diagnostic tests on a sheet, and continuously rolling the sheet between the outer layer and inner layer webs prior to the joining step.

The method of the above paragraph, wherein the positioning step involves providing a sheet on which the plurality of diagnostic tests are disposed, cutting the sheet into a plurality of patches, each patch including at least one of the diagnostic tests, and placing the plurality of patches into the plurality of cut-outs.

What is claimed is:

1. A health monitoring system, comprising:
a computing system configured to interact with a first diagnostic test associated with a first diaper, the first diagnostic test having one or more sensors configured to produce a first at least quasi-quantitative indication of a first set of one or more analytes contained in a first portion of bodily waste excreted by a subject in a first interval of time;
the computing system having one or more processors, a memory, and a health monitoring system program including a plurality of instructions stored in the memory that are executed by the one or more processors to instruct a data acquisition device to acquire automatically one or more digital images of the first at least quasi-quantitative indication, the one or more digital images not including a color comparison scale, to determine and select automatically by the one or more processors a focused first digital image from the acquired one or more digital images of the first at least quasi-quantitative indication, and to analyze the first digital image by comparing data derived from the first digital image of the first at least quasi-quantitative indication to a cluster, in the memory, the cluster based in part on different levels of brightness of the first digital image, in order to produce a first data point corresponding to the first at least quasi-quantitative indication;
the computing system being further configured to interact with a second diagnostic test associated with a second diaper, the second diagnostic test having one or more sensors configured to produce a second at least quasi-quantitative indication of a second set of one or more analytes contained in a second portion of bodily waste excreted by the subject in a second interval of time; and
wherein the plurality of instructions stored in the memory are also executed by the one or more processors to instruct the data acquisition device to acquire automatically one or more digital images of the second at least quasi-quantitative indication, to determine and select automatically by the one or more processors a focused second digital image from the acquired one or more digital images of the second at least quasi-quantitative indication, and to analyze the second digital image to produce a second data point based on the second at least quasi-quantitative indication, and to send a notification to a user if both the first and second data points correspond to an abnormal health condition of the subject.

2. The system of claim 1, wherein the first and second portions of bodily waste include respective first and second portions of urine, the abnormal health condition being diabetic ketoacidosis, and the plurality of instructions stored in the memory are also executed by the one or more processors to send the notification to the user if the first and second data points indicate that both of the first and second portions of urine contain at least one analyte that comprises one or both of a ketone or/and glucose.

3. The system of claim 1, wherein the first and second portions of bodily waste include respective first and second portions of urine, the abnormal health condition being a urinary tract infection, and the plurality of instructions stored in the memory are also executed by the one or more processors to send the notification to the user if the first and second data points indicate that both of the first and second portions of urine contain at least one analyte that comprises one or both of a nitrite or/and leukocyte esterase.

4. The system of claim 1, wherein the plurality of instructions stored in the memory are also executed by the one or more processors to visually read by the computing system a machine-readable code included in the first diagnostic test to direct the computing system to perform at least one task related to the production of the first data point.

5. The system of claim 4, wherein the at least one task includes at least one of:
determining whether the first diagnostic test has expired past a predetermined expiration date; and
determining an authenticity of the first diagnostic test.

6. The system of claim 1, wherein the plurality of instructions stored in the memory are also executed by the one or more processors to automatically acquire and transmit data corresponding to the first and second at least quasi-quantitative indications to an online service that is configured to automatically send the notification to the user via a handheld device.

7. The system of claim 1, wherein the plurality of instructions stored in the memory are also executed by the one or more processors to visually read by an optics system of the computing system a first machine-readable code indicia proximate the one or more sensors of the first diagnostic test to allow an application running on the computing system to perform at least one task related to a production of the first data point based on the first at least quasi-quantitative indication.

8. The system of claim 7, wherein the at least one task includes determining whether the first diagnostic test has expired past a predetermined expiration date.

9. The system of claim 8, wherein the at least one task further includes determining an authenticity of the first diagnostic test.

10. The system of claim 9, wherein the computing system includes an online service having a server and a database, the data acquisition device being a digital device having a second processor, a second memory and a camera that is configured to transmit the one or more digital images, the focused first digital image, and/or the first data point to the server for storage and/or analysis on the server.

11. The system of claim 7, further wherein the plurality of instructions stored in the memory are executed by the one or more processors to verify that each data point is associated with a unique diagnostic test and to discard any data points that correspond to a duplicated diagnostic test.

12. The system of claim 1, wherein the plurality of instructions stored in the memory are further executed by the one or more processors to:
receive and store a first digital data packet that includes a first sample reading, collected at the first interval of time, of the first diagnostic test associated with the first diaper configured to detect the first set of one or more analytes in the first portion of bodily waste excreted by the subject, wherein the first sample reading includes data corresponding to an amount of at least one analyte of the one or more analytes of the first set detected in the first diagnostic test and the first interval of time at which the first sample reading was collected;

receive and store a second digital data packet that includes a second sample reading, collected at the second interval of time different from the first interval of time, of the second diagnostic test associated with the second diaper, wherein the second sample reading includes data corresponding to an amount of at least one analyte of the one or more analytes of the second set detected and the second interval of time at which the second sample reading was collected, with the at least one analyte of the one or more analytes of the first set being the same analyte as the at least one analyte of the one or more analytes of the second set;

automatically compare the first and second sample readings against a standard for the at least one analyte that indicates normal and abnormal levels of the detected at least one analyte over different time intervals to analyze whether the first and second data readings correspond to the abnormal health condition of the subject based on the respective amounts of the at least one analyte detected in the respective first and second sample readings collected at the respective first and second intervals of time; and automatically transmit an indication configured for receipt at least by the data acquisition device if there is an abnormal level of the detected at least one analyte based on the analysis of the first and second sample readings.

13. The system of claim 12, wherein the one or more sensors of the first diagnostic test include a first sensor corresponding to the first set of analytes being detected, and the one or more sensors of the second diagnostic test include a second sensor corresponding to the same analyte as being detected by the first sensor or a different analyte than is being detected by the first sensor.

14. The system of claim 12, wherein the plurality of instructions stored in the memory are also executed by the one or more processors to indicate which analyte each of the first and second sensors are detecting.

15. The system of claim 1, wherein the plurality of instructions stored in the memory are also executed by the one or more processors to automatically acquire the one or more digital images of the first at least quasi-quantitative indication in response to instructions received from reading a first machine-readable code indicia of the first diagnostic test.

16. The system of claim 15, wherein the plurality of instructions stored in the memory are also executed by the one or more processors to individually color-correct first and second digital regions of the first digital image, the first digital region corresponding to a first region of the first diagnostic test that includes a first sensor and a uniform color reference material, the second digital region corresponding to a second region of the diagnostic test that is different from the first region and includes a second sensor and the reference material, wherein the individual color-correction is based in part on reading and analyzing a gradient in apparent color of the reference material in the first region and accordingly color correcting the first digital region, and of the reference material in the second region and accordingly color correcting the second digital region.

17. The system of claim 16, wherein the plurality of instructions stored in the memory are also executed by the one or more processors to independently color correct the first and second digital regions, based on the respective gradient of the reference material measured in the first and second digital regions as compared to a respective deviation of each respective gradient from a standard color of the reference material.

18. The system of claim 17, wherein the first diaper includes a reference material, a first sensor, and a second sensor, further wherein the reference material surrounds at least a portion of each of the first and second sensors.

19. The system of claim 17, wherein the plurality of instructions stored in the memory are also executed by the one or more processors to individually color-correct one or more of the first and second digital regions based at least in part on a color indication taken from a color corresponding to the first machine-readable code indicia based on the color of the first machine-readable code indicia being different than a color of the reference material and a color corresponding to true black.

20. The system of claim 17, wherein the plurality of instructions stored in the memory are also executed by the one or more processors to read the first machine-readable code indicia and automatically acquire the one or more digital images of the first at least quasi-quantitative indication when an alignment frame indicia associated with the data acquisition device is substantially aligned with an alignment frame indication received from the first diagnostic test.

21. The system of claim 20, wherein the plurality of instructions stored in the memory are also executed by the one or more processors to individually color-correct one or more of the first and second digital regions based at least in part on a color indication received that is associated with a color of an alignment frame of the first diagnostic test.

22. The system of claim 21, wherein the first diagnostic test includes an alignment frame, a first machine-readable code indicia, and a reference material, further wherein the color of the alignment frame of the first diagnostic test is different from the color of the first machine-readable code indicia and the color of the reference material.

23. The system of claim 20, wherein the first diagnostic test includes an alignment frame, a first sensor, a second sensor, and a first machine-readable code indicia, further wherein the first and second sensors and the first machine-readable code indicia are disposed within the alignment frame of the first diagnostic test.

24. The system of claim 17, wherein the plurality of instructions stored in the memory are also executed by the one or more processors to determine whether the first diagnostic test has expired past a first predetermined expiration date based on information indicating a predetermined expiration date of the first diagnostic test included in the first machine-readable code indicia.

25. The system of claim 1, wherein the plurality of instructions stored in the memory are also executed by the one or more processors to determine whether the second data point is a repeat of the first data point, and to exclude the second data point if determined to be repeated.

26. The system of claim 25, wherein the plurality of instructions stored in the memory are also executed by the one or more processors to automatically acquire the one or more digital images of the first at least quasi-quantitative indication in response to instructions received from reading a first machine-readable code indicia of the first diagnostic test and to automatically acquire the one or more digital images of the second at least quasi-quantitative indication in response to instructions received from reading a second machine-readable code indicia of the second diagnostic test, and determine if the second data point is a repeat of the first data point by comparing information received from the first and second machine-readable code indicia.

27. The system of claim 1, wherein the one or more digital images of the first at least quasi-quantitative indication includes a plurality of digital images.

28. The system of claim 1, wherein at least one of the one or more digital images of the first at least quasi-quantitative indication are acquired before the focused first digital image is determined and selected.

29. The system of claim 1, further wherein the plurality of instructions stored in the memory are executed by the one or more processors to grow the cluster by a clustering algorithm that includes k-means clustering.

30. The system of claim 1, further wherein the plurality of instructions stored in the memory are executed by the one or more processors to compare the one or more digital images of the at least quasi-quantitative indication to a standard not present in the one or more digital images.

31. A health monitoring system, comprising:
a computing system configured to interact with a first diagnostic test associated with a first diaper, the first diagnostic test having one or more sensors configured to produce a first at least quasi-quantitative indication of a first set of one or more analytes contained in a first portion of bodily waste excreted by a subject in a first interval of time;
the computing system having one or more processors, a memory, and a health monitoring system program including a plurality of instructions stored in the memory that are executed by the one or more processors to:
instruct a data acquisition device to acquire automatically one or more digital images of the first at least quasi-quantitative indication,
determine and select automatically by the one or more processors a focused first digital image from the acquired one or more digital images of the first at least quasi-quantitative indication,
individually color-correct first and second digital regions of the first digital image to generate a color-corrected first digital image, the first digital region corresponding to a first region of the first diagnostic test that includes a uniform color reference material and a first sensor of the one or more sensors of the first diagnostic test, the second digital region corresponding to a second region of the diagnostic test that is different from the first region and includes the reference material and a second sensor of the one or more sensors of the first diagnostic test, wherein the individual color-correction is based in part on reading and analyzing a gradient in apparent color of the reference material in the first region and accordingly color correcting the first digital region, and of the reference material in the second region and accordingly color correcting the second digital region, and
analyze the color-corrected first digital image to produce a first data point corresponding to the first at least quasi-quantitative indication;
the computing system being further configured to interact with a second diagnostic test associated with a second diaper, the second diagnostic test having one or more sensors configured to produce a second at least quasi-quantitative indication of a second set of one or more analytes contained in a second portion of bodily waste excreted by the subject in a second interval of time; and
wherein the plurality of instructions stored in the memory are also executed by the one or more processors to instruct the data acquisition device to acquire automatically one or more digital images of the second at least quasi-quantitative indication, to determine and select automatically by the one or more processors a focused second digital image from the acquired one or more digital images of the second at least quasi-quantitative indication, and to analyze the second digital image to produce a second data point based on the second at least quasi-quantitative indication, and to send a notification if both the first and second data points correspond to an abnormal health condition of the subject.

32. A health monitoring system, comprising:
a computing system configured to interact with a first diagnostic test associated with a first diaper, the first diagnostic test having one or more sensors configured to produce a first at least quasi-quantitative indication of a first set of one or more analytes contained in a first portion of bodily waste excreted by a subject in a first interval of time;
the computing system having one or more processors, a memory, and a health monitoring system program including a plurality of instructions stored in the memory that are executed by the one or more processors to:
instruct a data acquisition device to acquire automatically one or more digital images of the first at least quasi-quantitative indication when an alignment frame indicia associated with the data acquisition device is substantially aligned with an alignment frame indication received from the first diagnostic test,
determine and select automatically by the one or more processors a focused first digital image from the acquired one or more digital images of the first at least quasi-quantitative indication,
individually color-correct first and second digital regions of the first digital image to generate a color-corrected first digital image, the first digital region corresponding to a first region of the first diagnostic test that includes a uniform color reference material and a first sensor of the one or more sensors of the first diagnostic test, the second digital region corresponding to a second region of the diagnostic test that is different from the first region and includes the reference material a second sensor of the one or more sensors of the first diagnostic test, wherein the individual color-correction is based in part on reading and analyzing a gradient in apparent color of the reference material in the first region and accordingly color correcting the first digital region, and of the reference material in the second region and accordingly color correcting the second digital region, and
analyze the color-corrected first digital image to produce a first data point corresponding to the first at least quasi-quantitative indication;
the computing system being further configured to interact with a second diagnostic test associated with a second diaper, the second diagnostic test having one or more sensors configured to produce a second at least quasi-quantitative indication of a second set of one or more analytes contained in a second portion of bodily waste excreted by the subject in a second interval of time; and
wherein the plurality of instructions stored in the memory are also executed by the one or more processors to instruct the data acquisition device to acquire automatically one or more digital images of the second at least quasi-quantitative indication, to determine and select automatically by the one or more processors a focused second digital image from the acquired one or more digital images of the second at least quasi-quantitative indication, and to analyze the second digital image to produce a second data point based on the second at least quasi-quantitative indication, and to send a notification if both the first and second data points correspond to an abnormal health condition of the subject.

* * * * *